US011116721B2

(12) United States Patent
Baker et al.

(10) Patent No.: US 11,116,721 B2
(45) Date of Patent: Sep. 14, 2021

(54) PHARMACEUTICAL FORMULATIONS COMPRISING 4-{(1R)-2-[(6-{2-[(2,6-DICHLOROBENZYL)OXY]ETHOXY}HEXYL)AMINO]-1-HYDROXYETHYL}-2-(HYDROXYMETHYL) PHENOL

(75) Inventors: Darrell Baker, Middlesex (GB); Mark Bruce, Stevenage (GB); Marian Thomas, Ware (GB)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 13/148,982

(22) PCT Filed: Feb. 26, 2009

(86) PCT No.: PCT/EP2009/052306
§ 371 (c)(1),
(2), (4) Date: Aug. 11, 2011

(87) PCT Pub. No.: WO2010/097115
PCT Pub. Date: Sep. 2, 2010

(65) Prior Publication Data
US 2011/0319371 A1    Dec. 29, 2011

(51) Int. Cl.
*A61K 31/58*   (2006.01)
*A61K 31/138*  (2006.01)
*A61K 45/06*   (2006.01)
*A61K 9/00*    (2006.01)

(52) U.S. Cl.
CPC .......... *A61K 9/0075* (2013.01); *A61K 31/138* (2013.01); *A61K 31/58* (2013.01); *A61K 45/06* (2013.01)

(58) Field of Classification Search
CPC .... A61K 9/0075; A61K 31/138; A61K 31/58; A61K 45/06; A61K 2300/00
See application file for complete search history.

(56) References Cited

U.S. PATENT DOCUMENTS

| 4,778,054 | A | 10/1988 | Newell et al. |
| 4,811,731 | A | 3/1989 | Newell et al. |
| 4,832,880 | A | 5/1989 | Staniforth |
| 4,994,276 | A | 2/1991 | Baichwal et al. |
| 5,004,614 | A | 4/1991 | Staniforth |
| 5,035,237 | A | 7/1991 | Newell et al. |
| 5,135,757 | A | 8/1992 | Baichwal et al. |
| 5,145,684 | A | 9/1992 | Liversidge et al. |
| 5,376,386 | A | 12/1994 | Ganderton et al. |
| 5,441,060 | A | 8/1995 | Rose et al. |
| 5,478,578 | A | 12/1995 | Arnold et al. |
| 5,503,662 | A | 4/1996 | Berger |
| 5,506,203 | A | 4/1996 | Backstrom et al. |
| 5,560,490 | A | 10/1996 | Chawla |
| 5,590,645 | A | 1/1997 | Davies et al. |
| 5,626,871 | A | 5/1997 | Makino et al. |
| 5,642,728 | A | 7/1997 | Anderson et al. |
| 5,663,198 | A | 9/1997 | Reul et al. |
| 5,730,785 | A | 3/1998 | Idol et al. |
| 5,746,937 | A | 5/1998 | McKedy et al. |
| 5,829,434 | A | 11/1998 | Ambrosio et al. |
| 5,860,419 | A | 1/1999 | Davies et al. |
| 5,873,360 | A | 2/1999 | Davies et al. |
| 5,972,388 | A | 10/1999 | Sakon et al. |
| 6,032,666 | A | 3/2000 | Davies et al. |
| 6,103,141 | A | 8/2000 | Incorvia et al. |
| 6,119,853 | A | 9/2000 | Garrill et al. |
| 6,132,394 | A | 10/2000 | Lankinen |
| 6,153,224 | A | 11/2000 | Staniforth |
| 6,153,322 | A | 11/2000 | Lee et al. |
| 6,156,231 | A | 12/2000 | McKedy |
| 6,179,118 | B1 | 1/2001 | Garrill et al. |
| D440,874 | S | 4/2001 | Shurtleff et al. |
| 6,221,338 | B1 | 4/2001 | Staniforth |
| 6,279,736 | B1 | 8/2001 | Hekal |
| 6,303,991 | B1 | 10/2001 | Harper, Jr. et al. |
| 6,315,112 | B1 | 11/2001 | Garrill et al. |
| 6,321,747 | B1 | 11/2001 | Dmitrovic et al. |
| 6,352,152 | B1 | 3/2002 | Anderson et al. |
| 6,378,519 | B1 | 4/2002 | Davies et al. |
| 6,378,579 | B1 | 4/2002 | Giltner |
| 6,390,291 | B1 | 5/2002 | Garrill et al. |
| 6,521,260 | B1 | 2/2003 | Staniforth |
| 6,533,321 | B2 | 3/2003 | Class et al. |
| 6,536,427 | B2 | 3/2003 | Davies et al. |
| 6,537,983 | B1 | 3/2003 | Biggadike et al. |
| 6,582,678 | B2 | 6/2003 | Staniforth |
| 6,679,374 | B2 | 1/2004 | Garrill et al. |
| 6,759,398 | B2 | 7/2004 | Biggadike |
| 6,792,945 | B2 | 9/2004 | Davies et al. |
| 6,878,698 | B2 | 4/2005 | Biggadike et al. |
| 7,011,818 | B2 | 3/2006 | Staniforth |
| 7,101,866 | B2 | 9/2006 | Biggadike et al. |
| 7,186,401 | B2 | 3/2007 | Keller et al. |
| 7,225,808 | B2 | 6/2007 | Davies et al. |
| 7,337,593 | B2 | 3/2008 | Blum et al. |
| 7,361,787 | B2* | 4/2008 | Box et al. ........... 564/38 |
| 7,389,775 | B2 | 6/2008 | Davies et al. |
| 7,439,393 | B2* | 10/2008 | Box et al. ........... 564/38 |
| 7,488,827 | B2 | 2/2009 | Laine et al. |
| 7,498,440 | B2 | 3/2009 | Laine et al. |
| 7,501,011 | B2 | 3/2009 | Powers et al. |
| 7,549,272 | B2 | 6/2009 | DeFedericis |
| 7,629,335 | B2 | 12/2009 | Biggadike et al. |
| 7,776,895 | B2 | 8/2010 | Box et al. |

(Continued)

FOREIGN PATENT DOCUMENTS

| CA | 2347856 C | 5/2000 |
| DE | 10056855 A1 | 5/2002 |

(Continued)

OTHER PUBLICATIONS

Westmeier et al., "Combination Particles Containing Salmeterol Xinafoate and Fluticasone Propionate: Formulation and Aerodynamic Assessment," Journal of Pharmaceutical Sciences, vol. 97, No. 6, Jun. 2008.*

(Continued)

*Primary Examiner* — Kortney L. Klinkel
*Assistant Examiner* — William Y Lee
(74) *Attorney, Agent, or Firm* — James P. Riek

(57) ABSTRACT

Novel pharmaceutical formulations of a beta-2 agonist for inhaled administration via the nose or mouth, and methods of using them are provided.

67 Claims, No Drawings

(56) References Cited

U.S. PATENT DOCUMENTS

| | | | |
|---|---|---|---|
| 7,982,067 | B2 | 7/2011 | Box et al. |
| 8,183,257 | B2 | 5/2012 | Laine et al. |
| 8,309,572 | B2 | 11/2012 | Laine et al. |
| 8,511,304 | B2 | 8/2013 | Anderson et al. |
| RE44,874 | E | 4/2014 | Box et al. |
| 9,365,905 | B2 | 6/2016 | Newman et al. |
| 9,750,726 | B2 | 9/2017 | Baker et al. |
| 2003/0026766 | A1 | 2/2003 | Sanders |
| 2005/0121027 | A1 | 6/2005 | Nilsson et al. |
| 2005/0124644 | A1 | 6/2005 | Nilsson et al. |
| 2006/0134007 | A1 | 6/2006 | Krueger et al. |
| 2006/0144733 | A1 | 7/2006 | Wu et al. |
| 2006/0239932 | A1 | 10/2006 | Monteith et al. |
| 2006/0239933 | A1 | 10/2006 | Nilsson et al. |
| 2006/0257327 | A1 | 11/2006 | Zierenberg et al. |
| 2006/0269708 | A1 | 11/2006 | Merical et al. |
| 2007/0104655 | A1 | 5/2007 | Zierenberg et al. |
| 2007/0110678 | A1 | 5/2007 | Zierenberg et al. |
| 2007/0164254 | A1 | 7/2007 | Powers |
| 2007/0212422 | A1* | 9/2007 | Keller et al. .................. 424/498 |
| 2008/0003290 | A1 | 1/2008 | Box et al. |
| 2008/0063719 | A1 | 3/2008 | Morton et al. |
| 2009/0013998 | A1 | 1/2009 | Nilsson et al. |
| 2009/0029901 | A1 | 1/2009 | Wood-Kaczmar |
| 2009/0041682 | A1 | 2/2009 | Nilsson et al. |
| 2009/0152155 | A1 | 6/2009 | Pasbrig |
| 2009/0188495 | A1 | 7/2009 | Nilsson et al. |
| 2009/0192185 | A1 | 7/2009 | Nilsson et al. |
| 2009/0234929 | A1 | 9/2009 | Matsumoto |
| 2009/0298742 | A1 | 12/2009 | Roche et al. |
| 2011/0017615 | A1 | 1/2011 | Logel et al. |
| 2011/0269970 | A1 | 11/2011 | Box et al. |
| 2012/0309725 | A1 | 12/2012 | Baker et al. |
| 2014/0113888 | A1 | 4/2014 | Crater |
| 2015/0313841 | A1 | 11/2015 | Jones |
| 2016/0095840 | A1 | 4/2016 | Baker et al. |

FOREIGN PATENT DOCUMENTS

| | | | |
|---|---|---|---|
| DE | 202005002409 U1 | 7/2005 | |
| DE | 202005004659 U1 | 7/2005 | |
| EP | 0069715 A1 | 1/1983 | |
| EP | 0239798 B1 | 9/1990 | |
| EP | 466068 A1 | 1/1992 | |
| EP | 0328685 B1 | 5/1992 | |
| EP | 0824480 A1 | 2/1998 | |
| EP | 0606486 B1 | 8/2001 | |
| EP | 1232745 A1 | 8/2002 | |
| EP | 1240261 A1 | 9/2002 | |
| EP | 1241110 A1 | 9/2002 | |
| EP | 1243524 A2 | 9/2002 | |
| EP | 1131059 B1 | 3/2003 | |
| EP | 1691783 A1 | 8/2006 | |
| EP | 1292510 B1 | 2/2007 | |
| EP | 1232745 B1 | 3/2007 | |
| EP | 1883400 B1 | 10/2008 | |
| EP | 1990052 A1 | 11/2008 | |
| EP | 1991292 A1 | 11/2008 | |
| EP | 1827283 B1 | 2/2009 | |
| EP | 2127628 A1 | 12/2009 | |
| EP | 1626913 B1 | 2/2010 | |
| EP | 2277799 A1 | 1/2011 | |
| EP | 2283817 A1 | 2/2011 | |
| EP | 2283818 A1 | 2/2011 | |
| EP | 2954888 A1 | 12/2015 | |
| FR | 2660634 A1 | 10/1991 | |
| GB | 124009 | 3/1919 | |
| GB | 124010 | 3/1919 | |
| GB | 1242211 A | 8/1971 | |
| GB | 1381872 | 1/1975 | |
| GB | 1424432 | 2/1976 | |
| GB | 2064336 A | 6/1981 | |
| GB | 2129691 A | 5/1984 | |
| GB | 2169265 A | 7/1986 | |
| GB | 2178965 A | 2/1987 | |
| GB | 2242134 A | 9/1991 | |
| GB | 2269992 A | 3/1994 | |
| GB | 2410192 A | 7/2005 | |
| JP | 2002532216 A | 10/2002 | |
| WO | 87/05213 A1 | 9/1987 | |
| WO | 93/11746 A1 | 6/1993 | |
| WO | 95/00128 A1 | 1/1995 | |
| WO | 95/11666 A1 | 5/1995 | |
| WO | 1995032752 A1 | 12/1995 | |
| WO | 96/19199 A1 | 6/1996 | |
| WO | 96/23485 A1 | 8/1996 | |
| WO | 97/03649 A1 | 2/1997 | |
| WO | 99/38493 A1 | 8/1999 | |
| WO | 1999040031 A2 | 8/1999 | |
| WO | 99/53901 A1 | 10/1999 | |
| WO | 00/27363 A1 | 5/2000 | |
| WO | 00/28979 A1 | 5/2000 | |
| WO | 00/33811 A1 | 6/2000 | |
| WO | 2000037336 A1 | 6/2000 | |
| WO | 00/53157 A1 | 9/2000 | |
| WO | 00/53158 A1 | 9/2000 | |
| WO | 01/76575 A2 | 10/2001 | |
| WO | 01/78694 A2 | 10/2001 | |
| WO | 2001087731 A2 | 11/2001 | |
| WO | 2001097888 A2 | 12/2001 | |
| WO | 2001098174 A1 | 12/2001 | |
| WO | 2002012265 A1 | 2/2002 | |
| WO | 2002012266 A1 | 2/2002 | |
| WO | 02/43700 A2 | 6/2002 | |
| WO | 2002098874 A2 | 12/2002 | |
| WO | 03/024439 A1 | 3/2003 | |
| WO | 2003/024439 A1 | 3/2003 | |
| WO | WO 03/024439 * | 3/2003 | |
| WO | 2003057593 A1 | 7/2003 | |
| WO | 2003061743 A1 | 7/2003 | |
| WO | 2004000541 A1 | 12/2003 | |
| WO | 2004080808 A2 | 9/2004 | |
| WO | 2004101390 A1 | 11/2004 | |
| WO | 2004/110404 A1 | 12/2004 | |
| WO | 2004105727 A2 | 12/2004 | |
| WO | 2005/004845 A1 | 1/2005 | |
| WO | 2005004848 A1 | 1/2005 | |
| WO | 2005004853 A1 | 1/2005 | |
| WO | 2005037280 A1 | 4/2005 | |
| WO | 2005/046636 A1 | 5/2005 | |
| WO | 2005040304 A1 | 5/2005 | |
| WO | 2005044186 A2 | 5/2005 | |
| WO | 2005053644 A1 | 6/2005 | |
| WO | 2005053645 A1 | 6/2005 | |
| WO | 2005053646 A1 | 6/2005 | |
| WO | 2005053647 A1 | 6/2005 | |
| WO | 2005104745 A2 | 11/2005 | |
| WO | 2005115462 A1 | 12/2005 | |
| WO | 2005115463 A1 | 12/2005 | |
| WO | 2005115464 A1 | 12/2005 | |
| WO | 2005115465 A1 | 12/2005 | |
| WO | 2005115466 A1 | 12/2005 | |
| WO | 2005115467 A1 | 12/2005 | |
| WO | 2005123002 A1 | 12/2005 | |
| WO | 2006/008173 A2 | 1/2006 | |
| WO | 2006000758 A1 | 1/2006 | |
| WO | 2006023457 A1 | 3/2006 | |
| WO | 2006045715 A1 | 5/2006 | |
| WO | 2006062883 A2 | 6/2006 | |
| WO | 2006062931 A2 | 6/2006 | |
| WO | 2006071844 A2 | 7/2006 | |
| WO | 2006/108572 A2 | 10/2006 | |
| WO | 2006/124556 A2 | 11/2006 | |
| WO | 2005053648 | 11/2006 | |
| WO | 2006115264 A1 | 11/2006 | |
| WO | 2006135474 A1 | 12/2006 | |
| WO | 2007/012871 A1 | 2/2007 | |
| WO | 2007037748 A1 | 4/2007 | |
| WO | 2007042822 A2 | 4/2007 | |
| WO | 2007045378 A2 | 4/2007 | |
| WO | 2007057081 A1 | 5/2007 | |
| WO | 2007/068896 A1 | 6/2007 | |
| WO | 2007097451 A1 | 8/2007 | |
| WO | 2007102635 A1 | 9/2007 | |

(56) References Cited

FOREIGN PATENT DOCUMENTS

| | | |
|---|---|---|
| WO | 2007109606 A2 | 9/2007 |
| WO | 2007109698 A2 | 9/2007 |
| WO | 2007/117911 A2 | 10/2007 |
| WO | 2007109824 A1 | 10/2007 |
| WO | 2007121259 A2 | 10/2007 |
| WO | 2007/135024 A1 | 11/2007 |
| WO | 2008012338 A2 | 1/2008 |
| WO | 2008/021142 A2 | 2/2008 |
| WO | 2008014862 A1 | 2/2008 |
| WO | 2008040841 A1 | 4/2008 |
| WO | 2008/049842 A2 | 5/2008 |
| WO | 2008091968 A1 | 7/2008 |
| WO | 2008121321 A1 | 10/2008 |
| WO | 2008135570 A1 | 11/2008 |
| WO | 2009013243 A1 | 1/2009 |
| WO | 2009013244 A1 | 1/2009 |
| WO | 2009029029 A1 | 3/2009 |
| WO | 2009036243 A1 | 3/2009 |
| WO | 2009090010 A1 | 7/2009 |
| WO | 2009103336 A1 | 8/2009 |
| WO | 2009155387 A2 | 12/2009 |
| WO | 2010072354 A1 | 7/2010 |
| WO | 2010/097115 A1 | 9/2010 |
| WO | 2010097114 A1 | 9/2010 |
| WO | 2010135340 A2 | 11/2010 |
| WO | 2010038086 A3 | 4/2011 |
| WO | 2011067212 A1 | 6/2011 |
| WO | 2012168160 A1 | 12/2012 |
| WO | 2012168161 A1 | 12/2012 |
| WO | 2007/117911 A2 | 10/2017 |

OTHER PUBLICATIONS

Advair Diskus® Prescribing Information Aug. 2003.*
Advair® HFA Prescribing Information Jun. 2006.*
Kassem, Ph D Thesis "Generation of Deeply Inspirable Clouds from Dry Powder Mixtures" 1990.
Bossert, et al., "Effect of Mixing on the Lubrication of Crystalline Lactose by Magnesium Stearate" 1980; Drug Development and Industrial Pharmacy; vol. 6(6); pp. 573-589.
Ganderton, "The Generation of Respirable Clouds Form Coarse Powder Aggregates" 1992; Journal of Biopharmaceutical Sciences; vol. 3 (1/2); pp. 101-105.
Meakin, et al., "The Effect of Flow Rate on Drug Delivery from the Pulvinal, a High Resistance Dry Powder Inhaler" 1998; Journal of Aerosol Medicine; vol. 11 (3); pp. 143-152.
Ahmed, Ph D. Thesis "Particle Interactions in Multicomponent Systems" 1989.
Van Kamp, et al., "The Role of Water Uptake on Tablet Disintegration" 1986; Pharm Acta Helv; vol. 61 (1); pp. 22-29.
Peart, et al., "Multicomponent Particle Interactions in Dry Powder Aerosols" Nov. 1997; Pharmaceutical Research; Supplement-142; vol. 14 (11); para 1405.
PB62882EP document dated Feb. 14, 2013 re: Response to Communication dated Aug. 9, 2012.
PB62882EP official action dated Aug. 9, 2012.
PB62882EP Marked Claims Feb. 2013.
PB62882EP Unmarked Claims Feb. 2013.
Hannai, et al., The Efficacy and Safety of the Novel Long-Acting B2 Agonist Vilanterol in Patients with COPD; Jul. 1, 2012; Chest; vol. 142; pp. 119-127.
"PCT Application No. PCT/EP2009/052306, Notification of Withdrawal of Priority Claim" mailed Aug. 18, 2009.
Woodcock, et al., "Efficacy and Safety of Fluticason Furoate/Vilanterol Compared With Fluticasone Propionate/Salmeterol Combination in Adult and Adolescent Patients with Persistent Asthma" Chest; 2013; pp. 1222-1229; vol. 144, No. 4.
Busse, et al., "Expert Panel Report 3 (EPR-3): Guidelines for the Diagnosis and Managment of Asthma—Summary Report 2007" Allergy, Asthma & Immunology; 2007; pp. S94-S138; vol. 120, No. 5.

Dransfield, et al. "Efficacy and safety of once-daily fluticasone furoate/vilanterol (100/25 mcg) versus twice-daily fluticasone propionate/salmeterol (250/50 mcg) in COPD patients" Respiratory Medicine; 2014; pp. 1171-1179; vol. 108.
Vestbo, et al.,"Effectiveness of Fluticasone Furoate—Vilanterol for COPD in Clinical Practice" The New England Journal of Medicine; 2016; pp. 1253-1260; vol. 375.
Agusti, et al., "A comparison of the efficacy and safety of once-daily fluticasone furoate/vilanterol with twice daily fluticasone propionate/salmeterol in moderate to very severe COPD" Eur Respir J; 2014; vol. 43; pp. 763-772.
Global Initiative for the Diagnosis, Management and Prevention of Chronic Obstructive Pulmonary Disease, p. 14 (2016).
U.S. Appl. No. 13/819,149, filed Feb. 26, 2013.
U.S. Appl. No. 13/819,184, filed Feb. 26, 2013.
U.S. Appl. No. 13/819,184, "Non-Final Rejection" dated Apr. 16, 2018.
U.S. Appl. No. 13/819,184, "Applicant's Response to Non-Final Rejection of Oct. 2, 2017", dated Dec. 11, 2017.
U.S. Appl. No. 13/819,184, "Non-Final Rejection" dated Oct. 2, 2017.
Breo Ellipta Prescribing Information. May 2017. pp. 1-58.
Dransfield et al., "Once-daily inhaled fluticasone furoate and vilanterol versus vilanterol only for prevention of exacerbations of COPD: two replicate double-blind, parallel-group, randomized controlled trials", www.thelancet.com/respiratory, vol. 1, May 2003, pp. 210-223.
Siler et al., "A randomized, phase III trial of once-daily fluticasone furoate/vilanterol 100/25 mcg versus once-daily vilanterol 25 mcg to evaluate the contribution on lung function of fluticasone furoate in the combination in patients with COPD", Respiratory Medicine, 123, (2017), pp. 8-17.
Martinez et al., "Fluticasone furoate/vilanterol (100/25; 200/25 mcg) improves lung function in COPD: A randomized trial", Respiratory Medicine, (2013), 107, pp. 550-559.
Kerwin et al., "A randomised trial of fluticasone furoate/vilanterol (50/25 mcg; 100/25 mcg) on lung function in COPD", Respiratory Medicine, (2013) 107, pp. 560-569.
Vestbo et al., "Fluticasone furoate and vilanterol and survival in chronic obstructive pulmonary disease with heightened cardiovascular risk (SUMMIT): a double-blind randomize controlled trial" www.thelancet.com, vol. 387, Apr. 30, 2016, pp. 1817-1826.
Covelli et al., "Efficacy and safety of fluticasone furoate/vilanterol ortiotropium in subjects with COPD at cardiovascular risk", International Journal of COPD, (2016): 11, pp. 1-12.
Martinez et al., "Effect of Fluticasone Furoate and Vilanterol on Exacerbations of Chronic Obstructive Pulmonary Disease in Patients with Moderate Airflow Obstruction", Am J Respir Crit Care Med, vol. 195, issue 7, pp. 881-888, Apr. 1, 2017.
Caverly et al., "Fluticasone furoate, vilanterol and lung function decline in patients with moderate COPD and heightened cardiovascular risk", AJRCCM, pp. 1-25, Jul. 24, 2017.
EP1232745 Statement of Grounds of Appeal dated Mar. 25, 2010.
EP1232745 Decision of the Enlarged Board of Appeal in review procedure dated Jul. 30, 2012.
EP1232745 Written Submission in Preparation to/during Oral Proceedings dated Aug. 27, 2009, pp. 1-34.
EP1232745 Written Submission in Preparation to/during Oral Proceedings dated Aug. 27, 2009, pp. 1-4.
EP1232745 Written Submission in preparation to/during Oral Proceedings, pp. 1-33, dated Aug. 27, 2009.
EP1232745 Reply of the Patent Proprieter to the Notice(s) of Oppositions dated Oct. 9, 2008.
EP1232745 Reply of the Patent Proprieter to the Notice(s) of Oppositions dated Sep. 25, 2008.
EP1232745 Notice of Opposition dated Dec. 6, 2007.
EP1232745 Notice of Opposition dated Dec. 10, 2007.
EP2283817, Notice of Opposition dated Feb. 16, 2017, pp. 1-22.
EP2283817, Reply of the Patent Proprieter to the Notice(s) of Opposition dated Aug. 10, 2017.
Wade, A, et al., "Handbook of Pharmaceutical Excipients 2nd Edition" 1994; pp. 252-261; London: The Pharmaceutical Press.

(56) References Cited

OTHER PUBLICATIONS

Shur, J., et al., "From single excipients to dual excipient platforms in dry powder inhaler products." Intl' Journal of Pharmaceutics; 2016; p. 374; vol. 514.
The London Gazette, "Medicines Control Agency—Licenses Granted." Feb. 23, 2001; [https://www.thegazette.co.uk/notice/L-5613-1003].
Kawashima, et al., Design of inhalation dry powder of pranlukast hydrate to improve dispersibility by the surface modification with light anhydrous silicic acid (AEROSIL 200); Intl J of Pharmaceutics; 1998; pp. 243-251; vol. 173.
Naito, et al., "Applications of Comminution Techniques for the Surface Modification of Powder Materials" ISIJ International; 1993; pp. 915-924; vol. 33(9).
Staniforth, et al., "Interparticle forces in binary and ternary ordered powder mixes." J. Pharm. Pharmacol.; 1982 pp. 141-145; vol. 34.
Staniforth, et al. Abstract 1405 Pharmaceutical Research vol. 14 No. 11 (Supplement) Nov. 1997.
Fee, et al., "Influence of hydrophobic materials on dissolution of a nondisintegrating hydrophilic solid (potassium chloride)" JPharmSci; 1976; pp. 182-187; vol. 65.
Aulton, Michael E., "Pharmaceutics: The science of dosage form design." 1988; pp. 584-590.
EP1232745, Minutes of the Oral Proceedings (Opposition division), Oct. 27, 2009, pp. 1-10.
EP1232745, F3032 Notification of the Decision, pp. 1-23, dated May 18, 2011.
EP2283817, "Brief Communication—Opposition Proceedings, dated Jul. 14, 2017, pp. 1-6".
EP2283817, Brief Communication—Oral Proceedings, dated Aug. 28, 2018, pp. 1-164.
EP2283817, "Written Submission in Preparation to/during Oral Procedure" dated Aug. 23, 2010, pp. 1-31.
U.S. Appl. No. 14/970,945, Non-Final Rejection, dated Feb. 12, 2016.
U.S. Appl. No. 14/970,945, Response after Non-Final Rejection including claims and remarks, dated Jun. 10, 2016.
U.S. Appl. No. 14/970,945, Final Rejection, dated Aug. 24, 2016.
U.S. Appl. No. 14/970,945, Amendment After Final including claims and remarks, dated Oct. 24, 2016.
U.S. Appl. No. 14/970,945, Notice of Allowance, dated Jan. 11, 2017.
U.S. Appl. No. 14/970,945, Request for Examination including Arguments/Remarks and Claims, dated Apr. 11, 2017.
U.S. Appl. No. 14/970,945, Notice of Allowance, dated Apr. 20, 2017.
U.S. Appl. No. 14/970,945, Request for Continued Examination, dated Nov. 23, 2016.
Allen, et al., "Fluticasone Furoate, a Novel Inhaled Corticosteroid, Demonstrates Prolonged Lung Absorption Kinetics in Man Compared with Inhaled Fluticasone Propionate" Clin Pharmacokinet; 2013; pp. 37-42, vol. 52.
U.S. Appl. No. 15/678,246, filed Aug. 16, 2017.
U.S. Appl. No. 13/510,962, Response filed Apr. 14, 2015 to Office Action dated Jan. 14, 2015.
U.S. Appl. No. 14/651,988, Response filed Apr. 15, 2016 to Office Action dated Feb. 25, 2016.
U.S. Appl. No. 13/510,962, Response filed Aug. 20, 2014 to Office Action dated Jun. 20, 2014.
U.S. Appl. No. 13/510,962, Response filed Jun. 21, 2013 to Office Action dated Jun. 10, 2013.
U.S. Appl. No. 13/510,962, Response filed Mar. 10, 2014 to Office Action dated Oct. 9, 2013.
U.S. Appl. No. 14/124,276, Response filed May 2, 2016 to Office Action dated Feb. 2, 2016.
U.S. Appl. No. 14/651,988, Response filed Sep. 23, 2016 to Office Action dated Jun. 23, 2016.
U.S. Appl. No. 14/651,988, Notice of Allowance dated Nov. 16, 2016.
U.S. Appl. No. 13/510,962, Office Action dated Jan. 14, 2015.
U.S. Appl. No. 13/510,962, Office Action dated Jun. 16, 2015.
U.S. Appl. No. 13/510,962, Office Action dated Jun. 20, 2014.
U.S. Appl. No. 13/510,962, Office Action dated Oct. 9, 2013.
U.S. Appl. No. 14/124,276, Office Action dated Feb. 2, 2016.
U.S. Appl. No. 14/124,276, Office Action dated Jul. 6, 2016.
U.S. Appl. No. 14/651,988, Office Action dated Jun. 23, 2016.
U.S. Appl. No. 14/651,988, Office Action dated Feb. 25, 2016.
U.S. Appl. No. 13/510,962, filed Aug. 20, 2012.
U.S. Appl. No. 14/651,988, filed Jun. 12, 2015.
U.S. Appl. No. 15/678,246, Non-Final Rejection dated Sep. 5, 2018.
U.S. Appl. No. 15/678,246, Response to Restriction dated Feb. 1, 2018.
U.S. Appl. No. 15/678,246, Requirement for Restriction, Dec. 1, 2017.
Hanania, et al., "The Efficacy and Safety of the Novel Long-Acting B2 Agonist Vilanterol in Patients with COPD" Chest; 2012; pp. 119-127; vol. 142 (1).
OPP 1—Arven Opposition to European patent No. 2400950 to Glaxo Group Limited dated Feb. 14, 2020.
OPP 1 D2—Hanania, et al., "The Efficacy and Safety of the Novel Long-Acting Beta 2 Agonist Vilanterol in Patients with COPD." Chest; 2012; pp. 119-127; vol. 142(1).
OPP 2—Dehns Opposition to European patent No. 2400950 to Glaxo Group Limited dated Feb. 18, 2020.
OPP 1- D1—Submissions of the Proprietor in the examination proceedings related to the opposed Eur. Pat. Appl. 09 779 096.8-1219 dated Feb. 4, 2013; Response to Aug. 9, 2012 Communication.
OPP 2 D5—Biospace News Release: GlaxoSmithKline and Theravance, Inc. Announce Positive Phase 2b Results for Once-Daily Fluticason Furoate in the Treatment of Asthma, dated Feb. 4, 2009.
O2 D6—Fierce Biotech News Release: GSK and Theravance announce positive phase 2b results for LABA, '444 in the Horizon Asthma Development programme, dated Dec. 2, 2008.
OPP2 D7—Cazzola, et al., "Novel Long-acting bronchodilators for COPD and asthma." Brit J Pharm; 2008; pp. 291-299; vol. 155.
OPP 2 D8—Clinical Trial History of Changes for Study NCT00766090, Oct. 2, 2008.
OPP 3 D1—Clinical Trial Protocol for Clinical Trial with Identifier NCT00606684, Jan. 21, 2020.
OPP 3 D3—Declaration of Helsinki; Oct. 2008.
OPP 3 D4—Decision T 0007/07; Jul. 7, 2011.
OPP 3 D6—Decision T 0239/16; Sep. 13, 2017.
OPP 3 D7—NIH guidelines on Asthma Treatment; Aug. 28, 2007.
OPP 3 D9—Theravance Press Release dated Apr. 2, 2007.
OPP 3 D10—Donohue, "Minimal Clinically Important Differences in COPD Lung Function." COPD: Journal of Chronic Obstructive Pulmonary Disease; 2005; pp. 111-124; vol. 2.
DPP 3 D11—ICH Topic E 4 Dose Response Information to Support Drug Registration; European Medicines Agency Nov. 1994.
OPP 3/4—GJE Notice of Opposition to European patent No. 2400950 to Glaxo Group Limited dated Feb. 20, 2020.
OPP 3/4—AERA Notice of Opposition to European patent No. 2400950 to Glaxo Group Limited dated Feb. 20, 2020.
RD5410024, May 10, 2019, Anonymous.
"Rule 2 0.6 PCT Communication with Missing Pages and Drawings" PCT/EP2011/06055, filed Jan. 29, 2013.
"Fluticasone", www.Drugs.com, Wolters Kluwer Health (Wayback) (Jun. 4, 2009).
Aaron, S. et al., "Tiotropium in Combination with Placebo, Salmeterol, or Fluticasone-Salmeterol for Treatment of Chronic Obstructive Pulmonary Disease, A Randomized Trial," Annals of internal Medicine, pp. 545-556, W-144 , vol. 148 (8), Apr. 17, 2007 American College of Physicians.
Allen, A., et al. American Thoracic Society international Conference 2010, Ann Alien et al.: "Fluticasone furoate a novel inhaled corticosteroid demonstrates prolonged lung absorption kinetics in man" (Abstract).
Anderson, et al., "A Guide to the Measurement of Humidity", The Institute of Measurement and Control; 1996.
Angberg, M., et al., "Evaluation of heat-conduction microcalorimetry in pharmaceutical stability studies. IV. The influence of microcrystalline cellulose on the hydration rate of anhydrous lactose" 1991; International Journal of Pharmaceutics: vol. 77(2-3); pp. 269-277.

(56) References Cited

OTHER PUBLICATIONS

Annex, Submission dated Apr. 24, 2015 in the European patent application No. 11 755 042.6 filed by the same Applicant, cited in opposition of EP2611423.
Anonymous, "View of NCT01573624 on Jun. 4, 2012" ClinicalTrials. gov; 2012; pp. 1-4.
Anonymous, RD541024A, "Package for receiving medical device e.g. dry powder inhaler, has moisture absorbent unit absorbing gaseous and/or liquid substance in puch, where adsorbent unit includes chemically and biologically inert sachet comprising silica gel." May 10, 2009.
Australian Patent Application No. 2011 298 409, Applicant's Response to Examination Report dated Aug. 12, 2013, the response filed Oct. 22, 2013.
Australian Patent Application No. 2011 298 409, Examination Report dated Aug. 12, 2013.
Barnes, "Triple inhalers for obstructive airways disease: Will they be useful?" Expert. Review of Respiratory Medicine; 2011; vol. 5(3); pp. 297-300.
Bell, "A Beginner's Guide to Humidity Measurement", National Physical Laboratory; 2011.
Biggadike, K., "Letter To the Editor, Fluticasone furoate/fiuticasone propionate—different drugs with different properties" The Clinical Respiratory Journal 5:3, pp. 183-184 (2011) Print.
Bleecker, et al. "Consistently favorable safety profile of Fluticasone Furoate (FF), a once-daily (od) inhaled corticosteroid (ICS), across a range of treatment steps in patients with uncontrolled asthma", American Thoracic Society International Conference Abstracts: C31 Optimizing therapeutic strategies in airways disease, thematic poster session, May 15, 2011.
Busse, et al., "'Fluticasone Furoate (Ff), A Once-Daily Inhaled Corticosteroid (ICS). In efficacious in patients with uncontrolled asthma across a range of treatment steps", American Thoracic Society International Conference Abstracts: C31 Optimizing therapeutic strategies in airways disease, thematic poster session, May 15, 2011.
C Ray, Nicholas. Alcaraz, Lilian. "Muscarinic antagonist-B-adrenergic agonist dual pharmacology molecules as bronchodilators: a patent review". Expert Opin. Ther. Patents (2009) 19 (1): 1-12 published May 1, 2009.
Cazzola, M et al., "The scientific rationale for combining long-acting beta2-agonists and muscarinic antagonists in COPD", Pulmonary Pharmacology & Therapeutics, Academic Press, GB, vol. 23, No. 4, Aug. 1, 2010, pp. 257-267.
Clinica!Trials Identifier: NCT01128569 "A Randomised, Double-blind, Placebo-controlled, Three-way Crossover, Repeat Dose Pilot Study Comparing the Effect of inhaled Fluticasone Furoate/GW642444M Combination and Fluticasone Furoate on the Allergen-induced Early Asthmatic Response in Subjects With Mild Asthma";ClinicalTrials. gov archive: First received May 20, 2010; Last updated May 29, 2014.
ClinicalTrials Identifier: NCT01134042 "HZA1 06829: A Randomised, Double-blind, Parallel Group, Multicentre Study of Fluticasone Furoate/GW642444 inhalation Powder, Fluticasone Furoate inhalation Powder Alone, and Fluticasone Propionate Alone in the Treatment of Persistent Asthma in Adults and Adolescents" ClinicaiTriais.gov archive: First Yeceived May 27, 2010; Last updated Jun. 6, 2013.
Committee for medicinal products for human use: Guideline on the pharmaceutical quality of inhalation and nasal products, London, Jun. 21, 2006.
Communication of Notice of Opposition for EP Application No. 11755043.4 (Teva UK Ltd.) dated Apr. 1, 2016.
Communication of Notice of Opposition for EP Application No. 11755043.4 (Generics UK Limited) dated Mar. 31, 2016.
Communication of Notice of Opposition for EP Application No. 11755043.4 (Oser Andreas) dated Mar. 31, 2016.
Donohue et al., A randomized, double-blind dose-ranging study of the novel Lama GSK573719 in patients with COPD. RespirMed. Jul. 2012;106(7):970-9.
Donohue et al., Magnitude of umeclidinium/vilanterol lung function effect depends on monotherapy responses Results from two randomised controlled trials. Respir Med. Mar. 2016;112:65-74.
Donohue, et al., Efficacy and safety of once-daily umeclidinium/vilanterol 62.5/25 mcg in COPD. Respir Med. Oct. 2013; 107(1), pp. 1538-1546.
Eklirat Genuair™ 322 micrograms inhalation powder - Summary of Product Characteristics, Date submitted to PTO, Apr. 15, 2020.
El-Gendy et al., "Development of Budesonide NanoCluster Dry Powder Aerosols: Formulation and Stability." Journal of Pharmaceutical Sciences, vol. 101, No. 9 (Sep. 2012) pp. 3445-3455.
EP Patent No. 2611423, Patentee's Response to the Opposition dated Dec. 6, 2016.
Experimental data on relative humidity (patentee's submission of 19.02.2018, cited in opposition of EP2611423).
FDA Guidance Metered Dose inhaler (MD!) and Dry Powder Inhaler (DPI) Drug Products, Nov. 13, 1998 Chemistry, Manufacturing and Controls Documentations.
Fda Pulmonary Allergy Drugs Advisory Committee Meeting, Feb. 23, 2012, NOA 202-450 aclidinium bromide for the long-term, maintenance treatment of bronchospasm associated with chronic obstructive pulmonary disease (COPD), including chronic bronchitis and emphysema. (UMC292620). Retrieved from:https://www.fda.gov/downloads/AdvisoryCommittees/CommitteesMeetingMaterials/Drugs/Pulmonary-AllergyDrugsAdvisorvCommittee/UCM292620.pdf.
FDA, U.S. Food & Drug Administration, Tudorza™ Pressair™ US FDA Approved Product Label. Retrieved Online at: http://www.accessdata.fda.gov/scripts/cder/daf/index.cfm?event=BasicSearch.process (2012).
Ford, et al., "The therapeutic index of vilanterol trifenatate." Eur. Respir. J.; 2010; vol. 36, Suppl. 54: p. 1184.
Forest Pharmaceuticals, Highlights of Prescribing Information, Tudorza Pressair. (2012).
GlaxoSmithKline commences Reiovair Phase III asthma programme; https://US/gsk.com/en-US/media/press-releases/2010/glaxosmithkline-commences-reloviar-phase-lll-asthma-programme/; Dec. 17, 2015; pp. 1-13.
Glaxosmithkline, Evaluate the Safety, Efficacy and Dose Response of GSK573719 in Combination With Fluticasone Furoate in Subjects With Asthma {ILA115938), ClinicalTrials.gov Identifier NCT01573624, First Received Apr. 5, 2012, etrieved online at: hllps://clinicaltrials.gov/cl2/show/NCT01573624.
Glaxosmithkline, Highlights of Prescribing Information, Anoro Ellipta, FDA NDA 203975s003. (2016).
Grounds for the Decision (Annex)—Opposition, EP2611423, May 17, 2018, pp. 1-17.
GSK Annual Report, retrieved online at: http://annualreport.gsk.com/ (2015).
GSK Clinical Trial No. NCT01128569, Randomised Study Comparing the Effects of inhaled Fluticasone Furoate (FF)/Vilanteroi (VI; GW642444M) Combination and FF on an Allergen Induced Asthmatic Response, https://clinicaltrials. gov/ct2/show/study/NCT01128569?TERM=gW+642444m+fluticasone&rank=4; First received May 20, 2010; Last updated May 29, 2014; pp. 1-5.
Guchardi et al., Internationa! Journal of Pharmaceutics, vol. 348, Issues 1-2, Feb. 4, 2008, pp. 10-17.
Guidance for industry, "Metered dose inhaler (MDI) and dry powder inhaler (DPI) drug products, chemistry, manufacturing, and cold pulse documentation, graft guidance", US Department of Health and Human Services, Food and Drug Administration, Center for Drug Evaluation and Research (CDER), Oct. 1998.
Hajdu, D., et al., "Molecular Selves: Unique Moisture and Odor-Taste Control Material," Aug. 22-26, 1999; TAPPI Polymers, Laminations & Coatings Conference; Atlanta, vol. 2; pp. 655-662 (Abstract).
Hanania, et al., "Safety of vilanteroi trifenatate (VI) in a COPD dose-ranging study," Eur Respir J; 2010; vol. 36, Suppl, 54; p. 1185.
http://www.pharmpro. com/Archives/2006/10/Hamessing-The-Power-of-Desiccant-Technology-for-Inhalation-Therapies/, Date: 2006.
HygroPalm HP23-A/HP23-AW-A-Hand-Held Indicator User Guide, Rotronic AG; 2009-2012; pp. 1-39.
Statement of Grounds of Appeal, EP2611423, Sep. 26, 2018, Teva, pp. 1-15.

(56) References Cited

OTHER PUBLICATIONS

EP Patent No. 2400950, Opp 4 G/E Opposition Statement, Feb. 20, 2020.
OPP D50—B. Mei Jin Tanm L. Wah Chan and p. Wan Sia Heng, Chapter 11 Milling and Blending: Producing the Right Particles and Blend Characeristics for Dry Powder Inhalation Pharmaceutical Inhalation Aerosol Technology Third Edition 2019, p. 273-284.
OPP D58—print-out from https://www.gsk-studyregister.com/study?uniqueStudyId=B2C111045, Mar. 9, 2020.
OPP D61—print-out from https://www.gsk-studyregister.com/study?uniqueStudyId=B2C109575, Mar. 9, 2020.
OPP D64—print-out from https://www.gsk-studyregister.com/study?uniqueStudyId=HZC111348, Mar. 9, 2020.
U.S. Appl. No. 14/970,945, filed Dec. 16, 2015, Combinations of A Muscarinic Receptor Antagonist And A Beta-2 Adrenoreceptor Agonist.
Vaczek, "Dialing in stable packaging for sensitive drugs" Pharmaceutical and Medical Packaging News; 2010.
View of NCT01 128569 on Jun. 4, 2010, ClinicalTrials.gov archive [online], Jun. 4, 2010, [search at Apr. 30, 2014], URL.
View of NCT01134042 on Jul. 16, 2010, ClinicalTrials.gov archive [online], Jul. 16, 2010. [search at Apr. 30, 2014], URL.
Web Page of GSK Clinical Trial 1128569, dated May 20, 2010.
Welte, T et al., "Efficacy and Tolerability of Budesonide/Formoterol Added to Tiotropium in Patients with Chronic Obstructive Pulmonary Disease" Amer. J. Resp. & Critical Care Med. Vol. 180, pp. 741-750 (2009).
Wetterlim; "Turbuhaler: A New Powder inhaler for Administration of Drugs to the Airways"; Pharm. Res.; 1988; vol. 5 (8); pp. 506-508.
Williams, R.O., III, et al., "Investigation of moisture scavengers in pressurized metered-dose inhalers," 2000:S.T.P. Pharma Sciences; vol. 10(3); pp. 243-250 (Abstract).
World Health Organization, The top 10 causes of death. WHO Fact Sheet No. 310, retrieved online at: http://www.who.nl/mediacentre/factsheets/fs310/en/, Updated May 2014.
World Health Organization, WHO Technical Report Series, No. 953, 2009, Annex 2: Stability testing of active pharmaceutical ingredients and finished pharmaceutical products.
Written Submission in preparation to/during oral proceedings, EP2611423, Jan. 8, 2018, Dr. Andreas Oser, pp. 1-12.
Written Submission in preparation to/during oral proceedings, EP2611423, Jan. 8, 2018, Teva, pp. 1-15.
Young, et ai., "Influence of Humidity on the Electrostatic Charge and Aerosol Performance of Dry Powder Inhaler Barrier Based Systems." Pharmaceutical Research; May 2007; vol. 24, No. 5; pp. 963-970.
Zeng, "Particle Interactions in dry powder formulations for inhalation", Department of Pharmacy; King's College London: Chapters: pp. 131-173, 2001.
OPP D87—Drugs for the treatment of respiratory diseases, edited by D. Spina et al.; Cambridge University Press 2003.
OPP D88—Definition of the term "respiratory disease" downloaded on Feb. 12, 2020 from the online NCI Dictionary of Cancer Terms https://www.cancer.gov/publications/dictionaries/cancerterms/def/respiratory-disease.
U.S. Appl. No. 16/829,484, filed Mar. 25, 2020.
U.S. Office Action for U.S. Appl. No. 13/510,962, dated Jun. 10, 2013.
OPP D27—T950/13 3.03.01.
OPP D28—www.clinicaitrial.gov; identifier NCT00463697 dated Oct. 15, 2008 "A Randomized, Singiedose, Doseascending, Double Blind, Placebo-controlled, 5-way Crossover Study to investigate the Safety, Tolerability, Pharmacokinetics and Pharmacodynamics of inhaled Doses of GW642444M With Magnesium Stearate in Asthmatic Patients" Available from: https://clin icaltrials.gov/ct2/history/NCT00463697?V_ 5= View#StudyPage Top.
OPP D29—www.clinicaitrial.gov; identifier NCT00463697 dated Jul. 15, 2010 "A Randomized, Single-dose, Doseascending, Double Blind, Placebo-controlled, 5-way Crossover Study to investigate the Safety, Tolerability, Pharmacokinetics and Pharmacodynamics of Inhaled Doses of GW642444M With Magnesium Stearate in Asthmatic Patients" Available from: https://clinicaitrials.gov/ct2/history/NCT00463697?V_7 = View#StudyPage Top.
OPP D31—T712/13 03.03.01.
OPP D32—Ansel's Pharmaceutical Dosage Forms and Drug Delivery Systems, Eighth Edition, Eds. L.V. Allen, Jr et al., Lippincott Wiliams & Wilkins, 2005, chapters 2 and 6.
OPP D33—R. Schmidt "Dose-Finding Studies in Clinical Drug Development" Eur J Clin Pharmacol 1988, 34, 15-19.
OPP D34—Guideline for Industry Dose Response information to Support Drug Registration ICH-E4 FDA, Nov. 1994. Available from: https://www.fda.gov/regulatory-information/search-fdaguidance- documents.
OPP D35—BNF (British National Formulary), Sep. 2008, London, pp. 151-155.
OPP D36—*Actavis & Ors* v *ICOS & Or* [2017] EWCA Civ 1671.
OPP D37—*Actavis Group PTC EHF and others* v *ICOS Corporation and another* [2019] UKSC 15.
OPP D38—T1753/06 03.03.01.
OPP D39—Expert declaration provided by Mr Gary Muirhead; Feb. 18, 2020.
OPP D39A—Curriculum Vitae of Mr Gary Muirhead, Date Sumibbted to PTO: Apr. 15, 2020.
OPP D40- X. M. Zeng et al. Particle interactions in dry powder formulations for inhalation, Taylor & Francis, London and New York, 20301, Chapter 5, pp. 144-157, First Edition: Oct. 26, 2000.
OPP D41—www.clinicaltrial.gov; Identifier NCT00519376 dated Oct. 9, 2008 "A Randomised, Singledose, Dose Ascending, Double-blind, Placebo Controlled, Four-way, incomplete Block Crossover Study to Investigate the Safety, Tolerability, Pharmacokinetics and Pharmacodynamics of Inhaled Doses of GW642444M With Magnesium Stearate in COPD Patients" Available from: https://ciinicaltrials.gov/ct2/history/NCT005193767V _3= View#Study Page Top.
OPP D42—www.clinicaltrial.gov; Identifier NCT00606684 dated Nov. 6, 2008 "Study 8201 11045, A Dose-Finding Study of GW642444 Versus Placebo in Patients With COPD" Available from: https://clinicaltrials.gov/ct2/history/NCT00606684 ?V_ 11 = View#StudyPage Top.
OPP D44—S Newham Evolution of dry powder inhaler design, formulation, and performance, Res Med., v96,2002,293-294.
Opp D45—H. Chrystyn, "The Diskus™: a review of its position among dry powder inhaler devices", International Journal of Clinical Practice, 61,6, 1022-1036 , Jun. 2007.
Opp D46—S. Newman "How Well Do In Vitro Particle Size Measurements Predict Drug Delivery in Vivo?" Journal of Aerosol Medicine 1998, 11, S97-S104.
OPP D47—T. Peng, S. Lin, B. Niu, X. Wang, Y. Huang, X. Zhang, G. Li, X. Pan and C. Wu .Influence of physical properties of carrier on the performance of dry powder inhalers Acta Pharmaceutica Sinica B 2016, 6, 308-318.
OPP D48—N. Islam, P. Stewart, I. Larson and P. Hartley Effect of Carrier Size on the Dispersion of Salmeterol Xinafoate from Interactive Mixtures Journal of Pharmaceutical Sciences Apr. 2004, 93, 1030-1038.
OPP D49—V. N. P. Le, T. H. Hoang hi, E. Robins and M. P. Fiament, AAPS PharmSciTech Jun. 2012, 13, 477-484.
OPP D51—J. Shur, H. Harris, M. D. Jones, J. S. Kaergerand R. Price, The Role of Fines in the Modification of the Fluidization and Dispersion Mechanism Within Dry Powder inhaler Formulations Pharmaceutical Research Jul. 2008, 25, 1931-1940.
OPP D52—M, J, Telko and A. J. Hickey "Dry Powder Inhaler Formulation" Respiratory Care Sep. 2005, 50, 1209-1227.
OPP D53—S. J. Chariton "Agonist efficacy and receptor desensitization: from partial truths to a fuller picture" British Journal of Pharmacoloy 2009, 158, 165-168.
OPP D55—print-out from https://clinicaltrials.gov/ct2/show/NCT01147848, version dated Jan. 18, 2017.
OPP D56—print-out from https://clinicaltrials.gov/ct2/show/NCT00606684, version dated Feb. 1, 2008.
OPP D57—print-out from https://clinicaltrials.gov/ct2/show/NCT00606684, version dated Dec. 16, 2016.

(56) References Cited

OTHER PUBLICATIONS

OPP D58—print-out from https://www.gsk-studyregister.com/study?uniqueStudyId-B201 11045, Mar. 9, 2020.
OPP D59—print-out from https://clinicaitriais.gov/ct2/show/NCT00600171, version dated Jan. 22, 2009.
OPP D60—print-out from https://clinicaitriais.gov/ct2/show/NCT00600171, version dated Dec. 16, 2016.
OPP D62—print-out from https://clinicaitriais.gov/ct2/show/NCT00731822, version dated Aug. 8, 2008.
OPP D63—print-out from https://clinicaitriais.gov/ct2/show/NCT00731822, version dated Dec. 8, 2016.
OPP D64—print-out from https://www.gsk-studyregister.com/study?uniqueStudyId=HZC111348; Mar. 9, 2020.
OPP D65—print out from https://pipelinereview.com/index.php/2008122224291/Small-Molecules/GS Kand-Theravance-an nou nce-positive-phase-2b-results-for-LABA-444-in-the-treatment-of-COPD-in-the-Horizon-Development-Programme.html, press release dated Dec. 22, 2008.
OPP D66—print out from http //investor. i nva. com/news-releases/news-release-details/th eravance- reportsfourth-quarter-and-full-year-2008-results, press release dated Feb. 12, 2009.
OPP D67—B. Beilmann, R. Kubiak, P. Grab, H. Hausler and P. Langguth 11Effect of Interactive Ternary Mixtures on Dispersion Characteristics of Ipratropium Bromide in Dry Powder Inhaler Formulations AAPS PharmSciTech 2007 Apr. 20, 2007, 8, E1-E8.
OPP D68—S. Lawrence Lee, W. P. Adams, B. V. Li, D. P. Connr, B. A. Chowdhurry and L. X. Yu, In Vitro Considerations to Support Bioequivalence of Locally Acting Drugs in Dry Powder Inhalers for Lung Diseases The AAps Journal Sep. 3, 2009, 11,414-423.
OPP D71—print out from https ://www.ema.europa.eu/en/documents/scientific-guideline/note- guidanceclinical-investigation-medicinal-products-treatment-asthma_en.pdf, press release from Nov. 21, 2002.
OPP D72—print out from Belgian medicinal product register 2008 (Repertoire Commente Des Medicaments 2008).
OPP D75—Global Initiative for Chronic Obstructive Lung Disease (GOLD), "Global Strategy for the diagnosis, management, and prevention of chronic obstructive pulmonary disease" 2006, MCR Vision, Inc.
OPP D76 - Global Initiative for Asthma (GINA), "Global Strategy for Asthma Management and Prevention" 2008 (update).
OPP D77—M. Cazzola et al., Ultra long-acting j32-agonists in development for asthma and chronic obstructive pulmonary disease, Expert Opin. Investig. Drugs (2005) 14(7), pp. 775-783.
OPP D79—M. G. Matera et al., Ultra-long-acting j32-adrenoceptor agonists—an emerging therapeutic option for asthma and COPD?, Drugs 2007; 67(4), pp. 503-515.
OPP D82—USAN information vilanterol and vilanteroi trifenatate (downloaded on Feb. 13, 2020).
OPP D83—USAN information fluticasone furoate (downloaded on Feb. 13, 2020).
OPP D84—R. Kempsford et al.; The pharmacodynamics, pharmacokinetics and tolerability of repeat doses of the novel inhaled long-acting beta2 adrenoceptor agonist (Laba) GW642444 (25, 50 and 10 0 mcg) in healthy subjects; Am J Respir Crit Care Med 181; 2010:A4461.
Opp D86—US Pharmacopeia, USP 31 Vol. 1, pp. 605-607 as in force of May 1, 2008.
Jashnani et al., "Dry powder aerosol generation in different, environments: Performance comparisons of albuterol, albuterol sulfate, albuterol adipate and albuterol stearate", International Journal of Pharmaceutics; 1996; vol. 130; pp. 13-24.
Jashnani, et al., "Testing of dry powder aerosol formulations in different environmental conditions" International Journal of Pharmaceuticals; 1995; vol. 113; pp. 123-130.
Jones et al., Efficacy and safety of once-daily aclidinium in chronic obstructive pulmonary disease, Respiratory Research (2011), 12:55 httn://resniratorv-research.com/content/12/1/55.
Jones, P., Aclidinium Bromide Tiwice Daily for the Treatment of Chronic Obstructive Pulmonary Disease: A Review, Adv. Ther. (2013) , vol. 30, No. 4, pp. 354-368.
Laine, D. et al., "Discovery of Novel 1-Azoniabicyclo[2.2.2]octane Muscarinic Acetylcholine Receptor Antagonists" J. Med. Chem. 52(8), 2493-2505 (2009).
Laine, D. et al., "The pre-clinical pharmacology of the inhaled muscarinic antagonist GSK573719 predicts once-daily clinical dosing" Eur. Resp. Socy. Vol 38 Issue Suppl 55 (Sep. 1, 2011).
Lehto, et al., "Moisture Transfer into medicament chambers equipped with a double-barrier-desiccant, system", International Journal of Pharmaceutics; 2004; vol. 275 (1/2); 155-164.
Multisorb Technologies, "Multisorb Introduces Desiccant Integration Approaches to Preserve the Function of Respiratory Drug Devices and their Drug Product Formulations—New Generation of Multiform Coated Solid Form Sorbents Provide Enhanced Protection for Reservoir Dry Powder"; Jul. 1, 2007: http://multisorb.com/news-andevents/news/multisorb-introduces-desiccant-integration-approaches-to-preserve-the-function-of-respiratory-drug-devices-and-their-drug-product-formulations-new-generation-of-multiform-coated-solid-form-sorbents-provide-en].
U.S. Appl. No. 13/401,890, filed Feb. 22, 2012, Muscarinic Acetylcholine Receptor Antagonists.
Patent Proprietor's Reply to Appeal, EP2611423, Feb. 6, 2019, pp. 1-18.
Peters, et al., "Tiotropium Bromide Step-up Therapy for Adults with Uncontrolled Asthma" NE J of Med., 363(18), pp. 1715-1726 (Oct. 28, 2010).
Physician's Desk Reference, Thompson Reuters, 63rd edition, 2009, pp. 1276-1288, 1435-1440 and 1594-1601.
Possumato, Adrian. "New Pharmaceutical Applications Demand Intelligent Sorbents: Novel Formulations and Drug-Delivery Systems Require Optimized Packaging Protection" Oct. 2007; pp. 1-5.
Regulatory Dossier for Relvar Ellipta, pp. 1-6, cited in opposition of EP2611423, Feb. 19, 2018.
Relvar Ellipta device (patentee's submission of 19.02.201 8, cited in opposition of EP2611423).
Relvar Ellipta Package Leaflet; Jan. 2, 2019; pp. 1-12.
U.S. Appl. No. 12/353,436, filed Jan. 14, 2009, Muscarinic Acetylcholine Receptor Antagonists.
Reply of the Patent Proprietor to the Notice of Opposition for EP2611423, Dec. 6, 2016, pp. 1-49.
Response filed Oct. 24, 2016 to U.S. Office Action for U.S. Appl. No. 14/970,945, dated Aug. 24, 2016,.
Rosebraugh, Center for Drug Evaluation and Research, Approval Package for: Application No. 203975. Dec. 18, 2013.
Schelfhout et al., Activity of aclidinium bromide, a new long-acting muscarinic antagonist: a phase I study. Br J Clin Pharmacol. May 2010;69(5):458-64.
U.S. Appl. No. 13/819,149, Applicants' Amendment and Claims, dated Feb. 22, 2017.
U.S. Appl. No. 13/819,149, Applicant's response to Office Action of Mar. 6, 2015, dated Jun. 3, 2015.
U.S. Appl. No. 13/819,149, Final Office Action dated Jun. 20, 2014.
U.S. Appl. No. 13/819,149, Final Office Action dated Aug. 27, 2015.
U.S. Appl. No. 13/819,149, Final Rejection, dated Oct. 3, 2016.
U.S. Appl. No. 13/819,149, Non-final Office Action, dated Mar. 6, 2015.
U.S. Appl. No. 13/819,149, Non-Final Rejection dated Dec. 5, 2013.
U.S. Appl. No. 13/819,149, Request for Continued Examination filed Nov. 23, 2015.
U.S. Appl. No. 13/819,149, Request for Continued Examination filed Sep. 17, 2014,.
U.S. Appl. No. 13/819,149, Response to Restriction Requirement filed Oct. 21, 2013.
U.S. Appl. No. 13/819,149, Restriction Requirement dated Sep. 26, 2013.
U.S. Appl. No. 13/819,149, Claims and Applicants Arguments/Remarks Made in Amendment, filed Apr. 5, 2019.
U.S. Appl. No. 13/819,149, Non-Final Rejection, dated Jun. 2, 2019.
U.S. Appl. No. 13/819,184, Amendment filed dated Feb. 3, 2015.
U.S. Appl. No. 13/819,184, Final Rejection dated Nov. 7 , 2014.

(56) References Cited

OTHER PUBLICATIONS

U.S. Appl. No. 13/819,184, Non-Final Office Action dated Sep. 24, 2013.
U.S. Appl. No. 13/819,184, Non-Final Rejection dated May 1, 2014.
U.S. Appl. No. 13/819,184, Response to Non-Final Rejection filed Jul. 17, 2014.
U.S. Appl. No. 13/819,184, Response to Office Action filed Dec. 17, 2013.
Statement of Grounds of Appeal, EP2611423, Sep. 27, 2018, Dr. Andreas Oser, pp. 1-25.
Statement of Grounds of Appeal, EP2611423, Sep. 27, 2018, Generics UK, pp. 1-15.
Sterling, et ai., "Dose-Related Efficacy And Optimal Once-Daily (od) Dosing Interval Of The Long-Acting Beta2 Agonist(laba), Vilanterol Trifenatate (vi), In Adults With Persistent Asthma" Am J Respir Crit Care Med, May 17, 2011 C39 Novel Therapeutic Options in Airways Disease; Thematic Poster Session.
T 0805/93 (OP3's submission of 18.01.2018), opposition of EP2611423.
Telko, et al., "Dry Powder Inhaler Formulation" Respiratory Care; 2005; vol. 50, No. 9; pp. 1209-1227.
To, Masako, et al., "Fluticasone Furoate, A Novel Enhanced-affinity Inhaled Corticosteroid (ICS), Has More Potent Anti-inflammatory Effects Than Fluticasone Propionate in Peripheral Blood Mononuclear Ceils From Asthma and COPD Patients", Am J RespirCrit Care Med; 2010; vol. 181.
Opposition Submission to EP2400950 by HGF filed Feb. 21, 2020.
Opposition Statement EP2400950 by Sandoz filed Feb. 24, 2020.
Opposition Statement EP2400950 by Teva filed Feb. 22, 2020.
Opposition Statement EP2400950 by NLO filed Feb. 21, 2020.
Lotvall et al., "24hr Duration of the Novel Vilanterol Trifenatate in Asthma Patients Treated with Inhaled Corticosteroids" Eur Respir J., (2012) 40: pp. 570-579.
Sterling et al., "Efficacy and Optimal Dosing Internal of the Long Acting beta2-agonist vilanterol in persistent asthma: A Randomized Trial" Respiratory Medecine, (2012), 106, pp. 1110-1115.
ANORO Summary of product characteristics (SmPC) European Medicines Agency.
Barnes, P.J., BMJ vol. 333, Jul. 29, 2006, pp. 246-248.
Barnes, P.J., et al., Chest 2000, 117, 63S-66S.
Bateman et al., "Efficacy and safety of the long-acting muscarinic antagonist GSK233705 delivered once daily in patients with COPD", The Clinical Respiratory Journal, pp. 248-257, 2012.
Casarosa, et al., "Preclinical Evaluation of Long-Acting Muscarinic Antagonists: Comparison of Tiotropium and Investigational Drugs", The Journal of Pharmacology and Experimental Therapeutics, vol. 330, No. 2, pp. 660-668, 2009.
Cazzola, M et al., Emerging inhaled bronchodilators: an update. European Respiratory Journal 34.3 (2009) 757-769.
Cazzola, M et al., Drug Discovery Today: Therapeutic Strategies vol. 3, No. 3 2006, pp. 277-286.
Cazzola, "Aclidinium bromide, a novel long-acting muscarinic M3 antagonist for the treatment of COPD", Current Opinion in Investigational Drugs, 2009,10(5), pp. 482-490.
Cazzola, Current opinion: Pharmacological approaches in asthma and COPD; Breathe 6.1 (2009): 24-35.
Cazzola, et al., "Beta2-adrenoceptor agonists: current and future direction" British Journal of Pharmacology; 2011, vol. 163; pp. 4-17.
Clinical Study NCT00976144—Safety, Tolerability, Pharmacokinetic and Pharmacodynamic Effects of GSK573719 (LAMA) and GW642444 (LABA) Administered Individually and Concurrently in Healthy Japanese Subjects (DB2113208); Healthy Japanese Subjects (DB2113208); Jun. 26, 2017.
Decision of Technical Board of Appeal Mar. 3, 2002 T484/09.
EP2506844B1 GSK Response to Oppositions dated Apr. 29, 2019.
EU Approval of Eklira Genuair—Annex I, Summary of product characteristics; XP2780227.
FDA NOA 203975 Approval Letter Dec. 18, 2013.
FDA.gov details of Anoro Ellipta approved Dec. 18, 2013.

Global Initiative for Asthma (GINA) "The global strategy for asthma management and prevention" 2008 Medical Communications Resources Inc.
Global Initiative for Chronic Obstructive Lung Disease (GOLD) "The global strategy for the diagnosis, management, and prevention of chronic obstructive pulmonary diseases" 2009 Medical Communications Resouices Inc.
Gross, N.J., Anticholinergic agents in asthma and COPD; European Journal of Pharmacology 533.1-3 (2006): 36-39.
Gupta, A. et al., Difference in the lubrication efficiency of bovine and vegetable-derived magnesium stearate during tabletting; AAPS PharmSciTech 10.2 (2009): 500-504.
Kuna, et al., "Once-daily dosing with budesonide/formoterol compared with twice-daily budesonide/formoterol and once-daily budesonide in adult with mild to moderate asthma." Respiratory Medicine (2006) 100, 2151-2159.
Laine, D. et al., "Design, Synthesis, and Structure-Activity Relationship of Tropane Muscarinic Acetylcholine Receptor Antagonists", Journal of Medicinal Chemistry; vol. 52, pp. 5241-5252, 2009.
Letter of the USAN dated May 25, 2011 relating to umeclidinium.
Letter of the USAN dated May 25, 2011 relating to umeclidinium bromide.
Letter of the USAN dated Sep. 30, 2009 relating to vilanterol.
Letter of the USAN dated Sep. 30, 2009 relating to vilanterol trifenatate.
Opposition (EP2506844)—Dr. Markus Breuer, of Henkele Breuer & Partner, Filed Sep. 19, 2018.
Opposition (EP2506844)—Teva UK Limited, Filed Sep. 17, 2018.
Opposition (EP2508644)—Sima Patent Lisanslama Hizmettier Ltd STI, Filed Sep. 20, 2018.
Prat, et al., "Discovery of Novel Quaternary Ammonium Derivatives of (3R)-Quinuclidinol Esters as Potent and Long-Acting Muscarinic Antagonists with Potential for Minimal Systemic Exposure after Inhaled Adminislialion: Identification of (3R)-3-{[Hyroxy(di-2-thienyl)acetyl]oxy}-1-(3-phenoxypropyl)-1-azoniabicyclo[2.2.2]octane Bromide (Aclidinium Bromide)", Journal of Medicinal Chemistry, vol. 52, pp. 5076-5092, 2009.
Press release for ANORO US approval, Aug. 2, 2019.
Response filed Apr. 14, 2015 to U.S. Office Action for U.S. Appl. No. 13/510,962, dated Jan. 14, 2015.
EP2506844, Sep. 6, 2019 Reply of the patent proprietor to Jun. 17, 2019; opponent 1 submission.
Response filed Apr. 15, 2016 to U.S. Office Action for U.S. Appl. No. 14/651,988, dated Feb. 25, 2016.
Response filed Aug. 20, 2014 to U.S. Office Action for U.S. Appl. No. 13/510,962, dated Jun. 20, 2014.
Response filed Jun. 21, 2013 to U.S. Office Action for U.S. Appl. No. 13/510,962, dated Jun. 10, 2013.
Response filed Mar. 10, 2014 to U.S. Office Action for U.S. Appl. No. 13/510,962, dated Oct. 9, 2013.
Response filed May 2, 2016 to U.S. Office Action for U.S. Appl. No. 14/124,276, dated Feb. 2, 2016.
Response filed Sep. 23, 2016 to U.S. Office Action for U.S. Appl. No. 14/651,988, dated Jun. 23, 2016.
Umeclidinium Bromide; National Center for Biotechnology Information, PubChem Compound Database CID=1 1519069, http://pubchem.ncbi.nlm.nih.gOv/compound/11519069; Oct. 26, 2006.
MLANTEROL; National Center for Biotechnology Information, PubChem Compound Database; 2006; CI0=10184665, https://pubchem.ncbi.nim.nih.gov/compound/10184665.
Villetti et al., "Bronchodilator Activity of (3R)-3-[[[(3-fluorophenyl)[3,4,5- trifluorophenyl)methyl]amino] carbonyl] 3xy]-1-[2-oxo-2-(2-thienyl)ethyl]-1-azoniabicyclo[2.2.2] octane bromide (CHF5407), a Potent, Long-Acting, and Selective Muscarinic M3 Receptor Antagonist", The Journal of Pharmacology and Experimental Therapeutics, vol. 335, 10 3, pp. 622-635, 2010.
WHO Drug Information, vol. 22, No. 2, 2008, p. 132.
Wanzhen, et al., "Studies on muscarinic cholinergic receptors and anti-cholinergic therapy in chronic obstructive pulmonary disease," Chinese Journal of Tuberculosis and Respiratory Diseases, vol. 28, Issue 7, pp. 484-485, 2005.
U.S. Appl. No. 13/819,149 Non-Final Rejection dated Apr. 7, 2017.

(56) References Cited

OTHER PUBLICATIONS

U.S. Appl. No. 13/819,149 "Final Rejection Jan. 7, 2019".
U.S. Appl. No. 13/819,149 "Final Rejection" dated Oct. 20, 2017.
U.S. Appl. No. 13/819,149 "Non-Final Rejection" dated Mar. 6, 2015.
U.S. Appl. No. 13/819,149 "Non-Final Rejection" dated Mar. 30, 2016.
U.S. Appl. No. 13/819,149 "Non-Final Rejection"" dated Aug. 27, 2018".
"History of Changes for Study: NCT00606684, pp. 1-18, https://clinicaltrials.gov/ct2/hsitory/NCT006Q684, Jul. 7, 2020".
"Informed Consent Form, Clinical Trial Protocol B2C106996, pp. 1-16, Mar. 30, 2007".
P.J. Barnes "The Role of Anitcholinergics in Chronic Obstructive Pulmonary Disease" Am J. Medicine, 117(12A): 24S-32S (2004).
British National Formulary 58, Sep. 2009, RPS Publishing, London, p. 168.
Cazzola et al., "Outcomes for COPD pharmacological trials: from lung function to biomarkers", European Respiratory Journal 31 (2008), pp. 41-468.
Clinical Study NCT00606684 as downloaded from clinicaltrials.gov.
Clinical Study NCT00732472 as downloaded from clinicaltrials.gov.
Consent form concerning clinical study NCT00606684.
Consent form concerning clinical study NCT00732472.
Consent form concerning clinical study NCT00976144
GSK Press release relating to Trelegy Ellipta.
Rule 116 EPC submission, Opposition of EP 2506844, Appl. No. 10781527.6, by Teva UK Limited (Oppo 01), Jul. 23, 2020.
Rule 116 EPC submission, Opposition of EP 2506844, Appl. No. 10781527.6, by Dr. Markus Breuer (Oppo 02), Jul. 22, 2020.
Rule 116 EPC submission, Opposition of EP 2506844, Appl. No. 10781527.6, by Sima Patent Lisanslama Hizetleri Ltd STI (Oppo 03), Jul. 13, 2020.
Study report relating to clinical study NCT00976144 as downloaded from https://www.gsk-studyregister.com/en/.
Tai-Singer et al., "Initial assessment of single and repeat doses of inhaled umeclidiniumin patients with chronic obstructive pulmonary disease: Two randomised studies", European Journal of Pharmacology 701 (2013), pp. 40-48.
U.S. Appl. No. 13/819,149 "Response after Non-Final Action" dated Jun. 28, 2016.
U.S. Appl. No. 13/819,149 "Response after Non-Final Action" dated Jul. 6, 2017.
U.S. Appl. No. 13/819,149 "Response after Non-Final Action" dated Sep. 26, 2018.
U.S. Appl. No. 13/819,149 "Response after Non-Final Action" dated Feb. 26, 2014.
Haiyan, et al., "Development of the study on bronchodilators β2-adrenoceptor agonist," Chinese Journal of Medicinal Chemistry, vol. 14, No. 3; pp. 187-192; 2004.
Xi, Chronic Obstructive Pulmonary Disease and Heart Disease; 2008; pp. 101-107.
Chunseng, Practical Pharmacy; 2008; pp. 225-226.
Kempsford, et al., GW642444, a Novel Inhaled Long-acting Beta2 Adrenoceptor Agonist (LABA) at single doses of 25, 50 and 100 mcg, is well tolerated an demonstrates prolonged bronchodilation in COPD patients, Am. J. Respir. Crit. Care Med 181;2010:A4447.
Bnf.org; British National Formulary; 2009; pp. 613-614.

* cited by examiner

PHARMACEUTICAL FORMULATIONS COMPRISING 4-{(1R)-2-[(6-{2-[(2,6-DICHLOROBENZYL)OXY]ETHOXY}HEXYL)AMINO]-1-HYDROXYETHYL}-2-(HYDROXYMETHYL) PHENOL

This application is filed pursuant to 35 U.S.C. §371 as a United States National Phase Application of International Application No. PCT/EP2009/052306 filed Feb. 26, 2009.

FIELD OF THE INVENTION

This invention relates to pharmaceutical products and compositions for use in treating diseases mediated via the beta-2 adrenoreceptor, for example in the treatment and/or prophylaxis of respiratory diseases. More particularly this invention relates to novel compositions of the compound 4-{(1R)-2-[(6-{2-[(2,6-dichlorobenzyl)oxy]ethoxy}hexyl)amino]-1-hydroxyethyl}-2-(hydroxymethyl)phenol and pharmaceutically acceptable salts thereof and combinations thereof with other therapeutic agents, in particular 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate),
and the use of said compositions and combinations in medicine, particularly in the treatment of asthma and related disorders, such as the treatment of chronic obstructive pulmonary disease (COPD).

BACKGROUND OF THE INVENTION

Selective beta-2 adrenoreceptor agonists have been used in the prophylaxis and treatment of clinical conditions for which a bronchodilating agent has been indicated. Such conditions include diseases associated with airflow obstruction such as asthma, chronic obstructive pulmonary diseases (COPD) (e.g. chronic and wheezy bronchitis, emphysema), respiratory tract infection and upper respiratory tract disease (e.g. rhinitis, including seasonal and allergic rhinitis).

In particular, asthma and other related disorders are typically treated with beta-2 adrenergic receptor agonists (beta-2 agonists) as they provide a bronchodilator effect to the patient, resulting in relief from the symptoms of breathlessness. Within the beta-2 agonist class there are presently available short acting compounds for immediate relief, such as salbutamol, biltolterol, pirbuterol and terbutaline. There are also longer acting compounds commercially available, such as salmeterol and formoterol. Although salmeterol and formoterol are effective bronchodilators, in general their duration of action in human subjects is around 12 hours, hence twice daily dosing is generally required.

While the beta-2 agonists provide for symptomatic relief of bronchoconstriction in patients, another component of asthma, i.e. inflammation, often requires separate treatment. Typically, this treatment has been with a steroid. Currently available corticosteroids for use include beclomethasone dipropionate, budesonide, flunisolide, fluticasone propionate, mometasone furoate and triamcinolone.

WO 03/024439 describes compounds of the general formula:

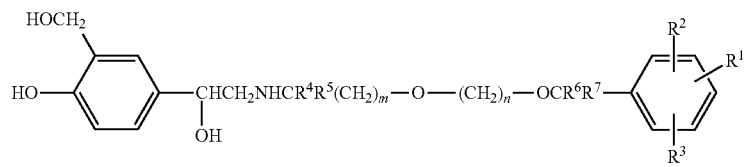

and salts, solvates, and physiologically functional derivatives thereof.

The compound 4-{(1R)-2-[(6-{2-[(2,6-dichlorobenzyl)oxy]ethoxy}hexyl)amino]-1-hydroxyethyl}-2-(hydroxymethyl)phenol is specifically described in WO03/024439, as are pharmaceutically acceptable salts thereof, in particular the acetate, triphenylacetate, α-phenylcinnamate, 1-naphthoate and (R)-mandelate salts.

WO02/12265 discloses the compound 6α, 9α-difluoro-17β-[(2-furanylcarbonyl)oxy]-11β-hydroxy-16α-methyl-3-oxo-androsta-1,4-diene-17β-carbothioic acid S-fluoromethyl ester.

SUMMARY OF THE INVENTION

In a first aspect the present invention provides a novel pharmaceutical formulation comprising a dry powder formulation of 4-{(1R)-2-[(6-{2-[(2,6-dichlorobenzyl)oxy]ethoxy}hexyl)amino]-1-hydroxyethyl}-2-(hydroxymethyl)phenol:

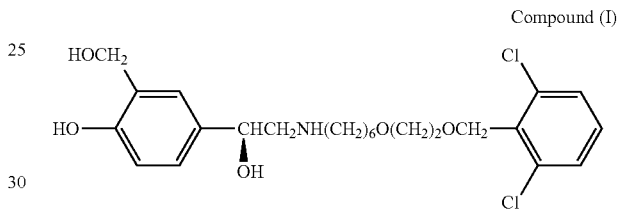

Compound (I)

or a pharmaceutically acceptable salt thereof
in admixture with a carrier such as lactose and a ternary agent such as magnesium stearate.

Hereinafter, Compound (I) may refer to the free base depicted above, and/or one or more salts thereof, as dictated by the context.

It will be appreciated that Compound (I) may exist in enantiomerically pure form or as a mixture of isomers, e.g. a racemic mixture.

In one embodiment Compound (I) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In another embodiment Compound (I) is 4-{(1R)-2-[(6-{2-[(2,6-dichlorobenzyl)oxy]ethoxy}hexyl)amino]-1-hydroxyethyl}-2-(hydroxymethyl)phenol α-phenylcinnamate.

In another embodiment the present invention provides a pharmaceutical product comprising:
a) a pharmaceutical formulation comprising 4-{(1R)-2-[(6-{2-[(2,6-dichlorobenzyl)oxy]ethoxy}hexyl)amino]-1-hydroxyethyl}-2-(hydroxymethyl)phenol or a pharmaceutically acceptable salt thereof (Compound I), a carrier such as lactose and a ternary agent such as magnesium stearate; and b) 6α, 9α-difluoro-17α-[(2-furanylcarbonyl)oxy]-11β-hydroxy-16α-methyl-3-oxo-androsta-1,4-diene-17β-carbothioic acid S-fluoromethyl ester

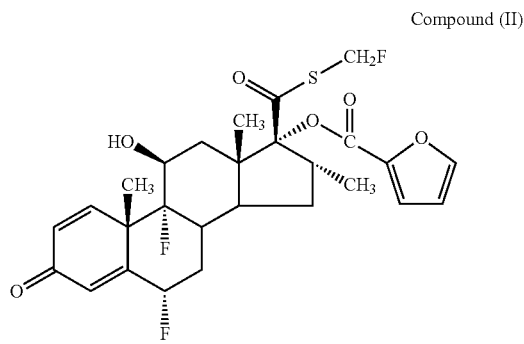

Compound (II)

This invention also provides for use of said pharmaceutical formulation and/or said pharmaceutical product in the manufacture of a medicament for the treatment and/or prophylaxis of respiratory diseases.

In one embodiment the use is for the manufacture of a medicament for the treatment of asthma and/or chronic obstructive pulmonary disease (COPD).

The invention also provides said pharmaceutical formulation and/or said pharmaceutical product for use in the treatment and/or prophylaxis of inflammatory or respiratory tract diseases, such as asthma and/or chronic obstructive pulmonary disease (COPD).

Another embodiment of the invention is a method for the treatment and/or prophylaxis of respiratory diseases, comprising administering to a patient in need thereof said pharmaceutical formulation or said pharmaceutical product comprising Compound (I) and Compound (II) wherein Compound (I) and Compound (II) are administered either sequentially or simultaneously.

In one embodiment of the invention the respiratory disease is selected from the group consisting of chronic obstructive pulmonary disease, chronic bronchitis, asthma, chronic respiratory obstruction, pulmonary fibrosis, pulmonary emphysema and allergic rhinitis.

DETAILED DESCRIPTION OF THE INVENTION

The present invention is directed to a pharmaceutical product comprising: 4-{(1R)-2-[(6-{2-[(2,6-dichlorobenzyl)oxy]ethoxy}hexyl)amino]-1-hydroxyethyl}-2-(hydroxymethyl)phenol:

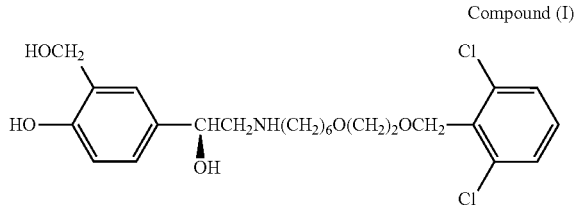

Compound (I)

or a pharmaceutically acceptable salt thereof.

To date, 4-{(1R)-2-[(6-{2-[(2,6-dichlorobenzyl)oxy]ethoxy}hexyl)amino]-1-hydroxyethyl}-2-(hydroxymethyl)phenol (and salts thereof) has been extensively tested in animal and human studies and has been found to demonstrate sustained bronchodilation over a 24 hour period in conjunction with a favourable safety profile and thus has the potential for once-daily administration.

In a first aspect the present invention provides a novel formulation comprising 4-{(1R)-2-[(6-{2-[(2,6-dichlorobenzyl)oxy]ethoxy}hexyl)amino]-1-hydroxyethyl}-2-(hydroxymethyl)phenol:

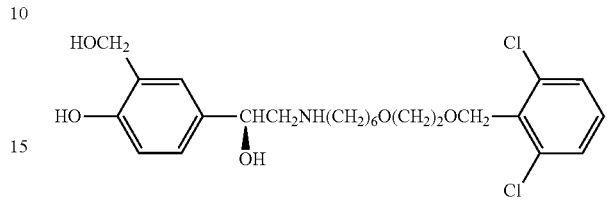

or a pharmaceutically acceptable salt thereof (Compound I), a carrier such as lactose and a ternary agent such as magnesium stearate.

Said formulation is suitable for topical delivery to the lung by inhalation, and may be administered by inhalation via the nose or mouth.

Formulations of Compound (I) with lactose and magnesium stearate have been found to demonstrate good levels of physical and chemical stability of the product, including at lower product strengths.

Said formulation may be prepared by any of the methods well known in the art of pharmacy. Such methods generally include the step of bringing the active ingredient into association with said carrier and ternary agent. Thus the formulations may be prepared by uniformly and intimately bringing into association Compound (I) with lactose and magnesium stearate. The formulation may be if desired filled into suitable unit dose forms.

Compound (I) is generally present in an amount of 0.020-3.0%, e.g. 0.024-0.8% by weight of the formulation wherein the weight of Compound (I) is calculated as the free base.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means e.g. by micronization. The desired fraction may be separated out by air classification or sieving. Preferably, the particles will be crystalline.

The carrier, e.g. lactose generally forms from 94-99%, e.g. 97.7-99.0% by weight of the formulation.

In general, the particle size of the carrier, for example lactose, will be much greater than the inhaled medicament within the present invention. When the carrier is lactose it will typically be present as milled lactose, wherein not more than 85% of lactose particles will have a MMD (mass median diameter) of 60-90 μm and not more than 15% will have a MMD of less than 15 μm.

In one embodiment the lactose is anhydrous lactose or lactose monohydrate.

Magnesium stearate is generally present in an amount of 0.2 to 2%, e.g. 0.6 to 2%%, e.g. 0.75%, 1%, 1.25% or 1.5%.

The magnesium stearate will typically have a particle size in the range 1 to 50 μm, and more particularly 1-20 μm, e.g. 1-10 μm. As is well known in the art stearic acid may comprise a mixture of stearic and palmitic acids; small amounts of other acids, e.g., lauric acid, myristic acid and/or arachic acid may also be present. Hence magnesium stearate similarly may comprise a mixture of salts formed with said acids. In general, the proportion of stearic acid present is 40.0 to 100%. Typically the proportion of stearic acid is present in an amount from 60 to 75% with the total proportion of stearic and palmitic acids in an amount from 90-100% e.g. 96-100%.

In one embodiment the aforesaid formulations comprise Compound (I), lactose and magnesium stearate.

In one embodiment the aforesaid formulations consist of Compound (I), lactose and magnesium stearate.

Pharmaceutically acceptable acid addition salts of Compound (I) include those formed from hydrochloric, hydrobromic, sulphuric, citric, tartaric, phosphoric, lactic, pyruvic, acetic, trifluoroacetic, triphenylacetic, phenylacetic, substituted phenyl acetic e.g., methoxyphenyl acetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, mandelic, cinnamic, substituted cinnamic (for example, methyl, methoxy, halo or phenyl substituted cinnamic, including 4-methyl and 4-methoxycinnamic acid and α-phenyl cinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids.

In one embodiment the pharmaceutically acceptable salt of Compound (I) is selected from the acetate, 1-naphthoate and (R)-mandelate salts.

In another embodiment the pharmaceutically acceptable salt of Compound (I) is the α-phenylcinnamate salt.

In another embodiment the pharmaceutically acceptable salt of Compound (I) is the triphenylacetate salt.

In one embodiment the invention provides a novel pharmaceutical formulation comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate, lactose and magnesium stearate.

In a further embodiment the invention provides a novel pharmaceutical formulation consisting of 4-{(1R)-2-[(6-{2-[(2,6-dichlorobenzyl)oxy]ethoxy}hexyl)amino]-1-hydroxyethyl}-2-(hydroxymethyl)phenol triphenylacetate, lactose and magnesium stearate.

In said formulations the specified components are generally present in the amounts specified hereinabove.

In one embodiment the invention provides a novel pharmaceutical formulation comprising 0.03-0.04% 4-{(1R)-2-[(6-{2-[(2,6-dichlorobenzyl)oxy]ethoxy}hexyl)amino]-1-hydroxyethyl}-2-(hydroxymethyl)phenol triphenylacetate, 94-99%, lactose and 0.75-1.25% magnesium stearate.

In one embodiment the invention provides a novel pharmaceutical formulation comprising 0.03-0.04% 4-{(1R)-2-[(6-{2-[(2,6-dichlorobenzyl)oxy]ethoxy}hexyl)amino]-1-hydroxyethyl}-2-(hydroxymethyl)phenol triphenylacetate, 97.7-99.0% lactose and 0.75-1% magnesium stearate.

As noted hereinabove, Compound (I) has been found to demonstrate sustained bronchodilation over a 24 hour period in conjunction with a favourable safety profile and thus is considered to have potential in the treatment of respiratory tract disease such as chronic obstructive pulmonary disease, chronic bronchitis, asthma, chronic respiratory obstruction, pulmonary fibrosis, pulmonary emphysema and allergic rhinitis.

Asthma is a chronic condition, which is characterised by widespread, variable and reversible airflow obstruction. Symptoms include coughing, wheezing, breathlessness and/or a tight feeling in the chest. Asthma attacks are generally caused by exposure to a trigger, such as pollen, dust or other allergens, which causes constriction of the airways (bronchoconstriction). It will be appreciated that a subject suffering from a condition such as asthma, may variously from time to time display no overt symptoms of the conditions, or may suffer from periodic attacks during which symptoms are displayed or may experience exacerbations or worsening of the condition. In this context the term 'treatment' is intended to encompass prevention of such periodic attacks or exacerbations of the existing condition. Such treatment may be referred to as 'maintenance treatment' or 'maintenance therapy'.

COPD is a chronic disease characterised by airways obstruction and reduced maximum expiratory flow from the lungs that manifests as persistent daily symptoms, such as shortness of breath (dyspnoea) and limitation of the ability to perform daily activities or exertion. Furthermore, there are periodic exacerbations of the condition that result in worsening of the day-to-day symptoms and activity limitation, and can also lead to hospitalisation of the patient because of the severity of the worsening symptoms/limitation. In addition, there is a progressive decline in lung function (disease progression) over several years.

Bronchodilator treatment in COPD includes but is not necessarily limited to reducing symptoms, particularly dyspnoea, to allow a patient to undertake more daily activities and other activities that require exertion, and preventing exacerbations.

Compound (I) may for example be administered by inhalation at a dose of from about 1 mcg to about 400 mcg/day (calculated as the free base). In one embodiment, formulations comprising Compound (I) and specifically 4-{(1R)-2-[(6-{2-[(2,6-dichlorobenzyl)oxy]ethoxy}hexyl)amino]-1-hydroxyethyl}-2-(hydroxymethyl)phenol triphenylacetate with a carrier such as lactose and a ternary agent such as magnesium stearate may be administered by inhalation at a dose of Compound (I) of from about 1 mcg to 100 mcg/day, for example 3, 6.25, 12.5, 25, 50 or 100 mcg/day (calculated as the free base). In one embodiment, Compound (I) may be administered by inhalation at a dose of 12.5 mcg/day. In another embodiment Compound (I) may be administered by inhalation at a dose of 25 mcg/day. In another embodiment Compound (I) may be administered by inhalation at a dose of 50 mcg/day. In general Compound (I) will be administered as a once-daily dose.

In one embodiment of this invention formulations of Compound (I) may be administered by means of various types of dry powder inhalers, for example, reservoir dry powder inhalers, unit-dose dry powder inhalers, pre-metered multi-dose dry powder inhalers, nasal inhalers or insufflators.

The formulations may be presented in unit dosage form. Dry powder compositions for topical delivery to the lung by inhalation may, for example, be presented in capsules and cartridges of for example gelatin, or blisters of for example laminated aluminium foil, for use in an inhaler or insufflator. Each capsule or cartridge may generally contain between 1 mcg and 400 mcg, e.g., between 1 mcg and 100 mcg of Compound (I).

Packaging of the formulation may be suitable for unit dose or multi-dose delivery. In one embodiment, a composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline. The DISKUS™ inhalation device is, for example, described in GB 2242134A.

A dry powder inhalable composition, may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline and HANDIHALER™ of Boehringer Ingelheim.

In a further embodiment the invention provides a formulation comprising Compound (I), a carrier, e.g. lactose and magnesium stearate in unit dose form. Each unit dose may generally contain between 1 mcg and 400 mcg, e.g., between 1 mcg and 100 mcg of Compound (I).

In a further embodiment the invention provides an inhaler containing a formulation comprising Compound (I), a carrier, e.g. lactose and magnesium stearate.

Compound (I) may be used in combination with one or more other therapeutic agents, such as inhaled corticosteroids and/or inhaled anticholinergic agents. Compound (I) and said other therapeutic agent(s) may be administered separately, sequentially or simultaneously in separate or combined pharmaceutical formulations. Thus Compound (I) and said other therapeutic agent(s) may be formulated separately and presented in separate packs or devices, or said individually formulated components may be presented in a single pack or device. Where appropriate, the individual compounds may be admixed within the same formulation, and presented as a fixed pharmaceutical combination. In general, such individual or admixed formulations of the compounds will also include pharmaceutical carriers or excipients.

In one embodiment Compound (I) may be used in combination with 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate)

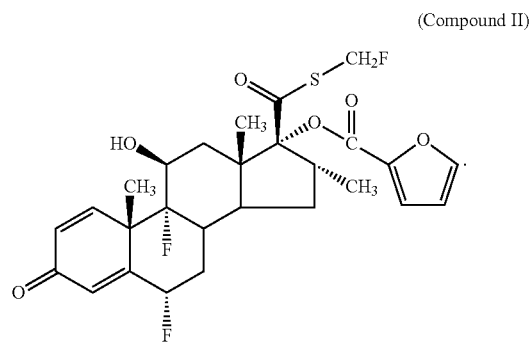

(Compound II)

Compound (II) has also been the subject of extensive studies in animal models and humans and has been found to be a long acting inhaled glucocorticosteroid which has potential for once-daily administration to the lungs.

Compound (II) is considered to have potential in the treatment of respiratory tract disease such as chronic obstructive pulmonary disease, chronic bronchitis, asthma, chronic respiratory obstruction, pulmonary fibrosis, pulmonary emphysema and allergic rhinitis.

Compound (II) may be presented as a formulation for inhalation, for example as described in WO02/12265. Thus for example Compound (II) may be presented as a dry powder formulation, optionally with a carrier or excipient, such as lactose or starch.

For use according to the present invention, Compound (II) may be administered by inhalation at a dose of from about 25 mcg to about 800 mcg daily, and if necessary in divided doses. Thus, the daily dose of compound (I) may be for example 25, 50, 100, 200, 300, 400, 600 or 800 mcg. In general Compound (II) will be administered as a once-daily dose.

Compound (II) may be provided in unit dose form, for example as described for Compound (I). Each unit dose of Compound (II) may contain between 25 and 800 mcg.

In a further aspect the present invention provides a dry powder formulation comprising 4-{(1R)-2-[(6-{2-[(2,6-dichlorobenzyl)oxy]ethoxy}hexyl)amino]-1-hydroxyethyl}-2-(hydroxymethyl)phenol or a pharmaceutically acceptable salt thereof (Compound I), a carrier such as lactose and a ternary agent such as magnesium stearate, in combination with 6α, 9α-difluoro-17β-[(2-furanylcarbonyl)oxy]-11β-hydroxy-16α-methyl-3-oxo-androsta-1,4-diene-17β-carbothioic acid S-fluoromethyl ester (Compound II).

In one embodiment said combination may be presented in the form of a pack comprising a dry powder formulation of 4-{(1R)-2-[(6-{2-[(2,6-dichlorobenzyl)oxy]ethoxy}hexyl)amino]-1-hydroxyethyl}-2-(hydroxymethyl)phenol or a pharmaceutically acceptable salt thereof (Compound I) in admixture with a carrier such as lactose and a ternary agent such as magnesium stearate and a separate formulation of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (Compound II).

Said pack may comprise two separate inhaler devices, containing respectively the separate formulations of Compound (I) and Compound (II). Inhaler devices for delivery of Compound (II) include those described hereinabove for delivery of Compound (I).

Said pack may also comprise a delivery device which permits separate containment of Compound (I) and Compound (II) optionally in admixture with one or more excipients. Thus, for example, the individual compounds of the combination are administrable simultaneously but are stored separately, e.g., in separate pharmaceutical compositions, for example as described in WO2003/061743 A1, WO2007/012871 A1 and/or WO2007/068896. In one embodiment a delivery device permitting separate containment of actives is an inhaler device having two medicament packs in peelable blister strip form, each pack containing pre-metered doses in blister pockets arranged along its length. Said device has an internal indexing mechanism which, each time the device is actuated, peels opens a pocket of each strip and positions the packs so that each newly exposed dose of each pack is adjacent a manifold which communicates with a mouthpiece of the device. When the patient inhales at the mouthpiece, each dose is simultaneously drawn out of its associated pocket into the manifold and entrained via the mouthpiece into the patient's respiratory tract. Thus, each time the device is used, the patient is administered a combination therapy consisting of a dose from each medicament pack.

A further device that permits separate containment of different compounds is DUOHALER™ of Innovata.

The present invention further provides a pharmaceutical formulation comprising a combination of Compound (I) and Compound (II) wherein at least Compound (I) is formulated with magnesium stearate.

In a further aspect the present invention provides a novel pharmaceutical product comprising
(a) a dry powder formulation of 4-{(1R)-2-[(6-{2-[(2,6-dichlorobenzyl)oxy]ethoxy}hexyl)amino]-1-hydroxyethyl}-2-(hydroxymethyl)phenol or a pharmaceutically acceptable salt thereof (Compound I) in admixture with a carrier such as lactose and a ternary agent such as magnesium stearate, and
(b) a dry powder formulation of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (Compound II).

In one embodiment on the invention, Compound (I) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In a yet further aspect there is provided a delivery device containing as separate formulations:
(a) a dry powder formulation comprising 4-{(1R)-2-[(6-{2-[(2,6-dichlorobenzyl)oxy]ethoxy}hexyl)amino]-1-hydroxyethyl}-2-(hydroxymethyl)phenol or a pharmaceutically acceptable salt thereof (Compound I), a carrier such as lactose and a ternary agent such as magnesium stearate, and
(b) a dry powder formulation comprising 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (Compound II).

In one embodiment of this invention, Compound (I) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In general each of the therapeutic agents described herein may be employed in enantiomerically pure form, but it will be appreciated that the invention extends to mixture of isomers e.g. a racemic mixture, in relation to either or both of said therapeutic agents.

This invention also provides for use of a formulation comprising a compound (I), a carrier such as lactose and a ternary agent such as magnesium stearate, in the manufacture of a medicament for in treating diseases mediated via the beta-2 adrenoreceptor, for example in the treatment and/or prophylaxis of respiratory diseases.

In one embodiment the use is for the manufacture of a medicament for the treatment and/or prophylaxis of respiratory diseases.

In another embodiment the use is for the manufacture of a medicament for the treatment of asthma and/or chronic obstructive pulmonary disease (COPD).

This invention also provides for use of a formulation comprising a Compound (I), a carrier such as lactose and a ternary agent such as magnesium stearate, in combination with a compound (II) in the manufacture of a medicament for treating diseases mediated via the beta-2 adrenoreceptor, for example in the treatment and/or prophylaxis of respiratory diseases.

In one embodiment the use is for the manufacture of a medicament for the treatment and/or prophylaxis of respiratory diseases, by simultaneous or sequential administration of Compound (I) and Compound (II).

In another embodiment the use is for the manufacture of a medicament for the treatment of asthma and/or chronic obstructive pulmonary disease (COPD) by simultaneous or sequential administration of Compound (I) and Compound (II).

The invention also provides a formulation comprising a compound (I), a carrier such as lactose and a ternary agent such as magnesium stearate, for use in the treatment and/or prophylaxis of inflammatory or respiratory tract diseases, such as asthma and/or chronic obstructive pulmonary disease (COPD).

The invention also provides a formulation comprising a compound (I), a carrier such as lactose and a ternary agent such as magnesium stearate, in combination with Compound (II) for use in the treatment and/or prophylaxis of inflammatory or respiratory tract diseases, such as asthma and/or chronic obstructive pulmonary disease (COPD).

Another embodiment of the invention is a method for the treatment and/or prophylaxis of inflammatory or respiratory tract diseases, which method comprises administering to a patient in need thereof, a pharmaceutical product comprising a formulation comprising a compound (I), a carrier such as lactose and a ternary agent such as magnesium stearate.

Another embodiment of the invention is a method for the treatment and/or prophylaxis of inflammatory or respiratory tract diseases, which method comprises administering either sequentially or simultaneously, to a patient in need thereof, a pharmaceutical product comprising a formulation comprising a compound (I), a carrier such as lactose and a ternary agent such as magnesium stearate, and Compound (II).

In one embodiment of the invention the respiratory disease is selected from the group consisting of chronic obstructive pulmonary disease, chronic bronchitis, asthma, chronic respiratory obstruction, pulmonary fibrosis, pulmonary emphysema and allergic rhinitis.

In another embodiment of the invention the pharmaceutical product may be used for the treatment of respiratory disease, and more specifically the treatment of asthma and/or chronic obstructive pulmonary disease (COPD), by simultaneous or successive administration of Compound (I) and Compound (II).

6α, 9α-Difluoro-17α-[(2-furanylcarbonyl)oxy]-11β-hydroxy-16α-methyl-3-oxo-androsta-1,4-diene-17β-carbothioic acid S-fluoromethyl ester may be prepared as described in WO 2002/12265.

4-{(1R)-2-[(6-{2-[(2,6-dichlorobenzyl)oxy]ethoxy}hexyl)amino]-1-hydroxyethyl}-2-(hydroxymethyl)phenol, and its salts, including 4-{(1R)-2-[(6-{2-[(2,6-dichlorobenzyl)oxy]ethoxy}hexyl)amino]-1-hydroxyethyl}-

2-(hydroxymethyl)phenol triphenylacetate may be prepared as described in WO 2003/024439.

Clinical Studies of Compound (I) and Compound (II)

Compound (I) as the α-phenylcinnamate salt and the triphenylacetate salt has been studied in a number of clinical pharmacology studies, including single- and repeat-dose studies. In addition, these studies have evaluated Compound (I) with the excipients cellobiose octaacetate and magnesium stearate.

In asthmatic patients, a statistically and clinically significant improvement in trough (24-hour) FEV1 was observed for all doses of Compound (I) compared to placebo. Single doses of 25 mcg to 100 mcg of Compound (I) triphenylacetate (containing lactose and magnesium stearate) demonstrated 24 hour duration of action as assessed by a 200 mL or greater increase in mean 23 to 24 hour post-dose FEV1 versus placebo.

In one study in asthmatic patients 100 mcg of Compound (I) triphenylacetate formulated with lactose and magnesium stearate has shown a favourable onset of action.

In COPD patients, treatment with 100 mcg and 400 mcg Compound (I) alpha-phenylcinnamate (with lactose alone) achieved a clinically relevant adjusted mean difference from placebo in weighted mean trough $FEV_1$ (22 to 24 hrs) of >100 mL. Single doses of 25 mcg to 100 mcg of Compound (I) triphenylacetate (containing lactose and magnesium stearate) demonstrated 24 hour duration of action as assessed by a 190 mL or greater increase in mean 23 to 24 hour post-dose FEV1 versus placebo).

Compound (II) has been studied in a number of clinical pharmacology studies, including single- and repeat-dose studies and at a range of doses. In addition, these studies have evaluated Compound (II) with the excipients cellobiose octaacetate and magnesium stearate.

In asthmatic patients, a statistically and clinically significant improvement in trough (24-hour) FEV1 was observed at doses of from 100 to 400 mcg Compound (II) compared to placebo.

A study has also been carried out to evaluate the pharmacodynamics and pharmacokinetics of Compound (I) and Compound (II) when administered separately and in combination as a single dose from a novel dry powder device in healthy subjects.

Pharmaceutical Formulations

Preparation of Blends

Pharmaceutical grade lactose monohydrate complying with the requirements of Ph.Eur/USNF was used. Before use, the Lactose Monohydrate was sieved through a coarse screen (mesh size 800 microns) to deaggregate the material. Compound (I) triphenylacetate was micronised before use in an APTM microniser to give a MMD (mass median diameter) of from 2 to 5 microns.

Pharmaceutical grade magnesium stearate, complying with the requirements of Ph.Eur/NF was used as supplied with a mass median particle size <10 microns.

The magnesium stearate (typically 130 g) was combined with lactose monohydrate and blended using either a high shear mixer (a QMM, PMA or TRV series mixer) or a low shear tumbling blender (a Turbula mixer) to provide a magnesium stearate/lactose premix, hereinafter referred to as blend A.

Final blend B was obtained by first pre-mixing an appropriate quantity of blend A with compound (I) triphenylacetate (typically 5-165 g) using either a high shear mixer (a QMM, PMA or TRV series mixer) or a low shear tumbling blender (a Turbula mixer) and then blending that blend A/compound (I) triphenylacetate premix with further blend A in a weight ratio appropriate to provide blend B containing the magnesium stearate in the required quantity. Compound (I) triphenylacetate was combined with lactose monohydrate and blended using a high shear TRV series mixer. The final concentration of compound (I) triphenylacetate in the blends was typically in the range 0.02% w/w—0.8% w/w free base equivalent.

The blended composition was transferred into blister strips (typical nominal mean quantity of blend B per blister is 12.5-13.5 mg) of the type generally used for the supply of dry powder for inhalation and the blister strips were sealed in the customary fashion.

Using the above-described procedure the following exemplary formulations were prepared:

| Blend No | Mass of Magnesium stearate | Mass of compound (I) triphenylacetate (micronised)[1] | Mass of lactose | Quantity per blister |
|---|---|---|---|---|
| 1 | 130 g | 5.0 g | To 13 kg | 13 mg |
| 2 | 130 g | 10.3 g | To 13 kg | 13 mg |
| 3 | 130 g | 20.7 g | To 13 kg | 13 mg |
| 4 | 130 g | 41.3 g | To 13 kg | 13 mg |
| 5 | 130 g | 82.7 g | To 13 kg | 13 mg |
| 6 | 130 g | 165.4 g | To 13 kg | 13 mg |

[1]The quantity of compound (I) triphenylacetate used is based on a base to salt conversion factor of 1.59

The invention claimed is:

1. A pharmaceutical product consisting essentially of:
    (a) a dry powder formulation consisting essentially of Compound (I), which is 4-{(1R)-2-[(6-{2-[(2,6-dichlorobenzyl)oxy]ethoxyl}hexyl)amino]-1-hydroxyethyl}-2-(hydroxymethyl)phenol or a pharmaceutically acceptable salt thereof, present in micronized form and in a dose selected from the group consisting of 12.5, 25, and 50 mcg, calculated as the free base, and wherein Compound (I) is in admixture with lactose and 0.6 to 2% w/w of magnesium stearate, and
    (b) a dry powder formulation consisting essentially of Compound (II), which is 6α, 9α-difluoro-17α-[(2-furanylcarbonyl)oxy]-11β-hydroxy-16α-methyl-3-oxo-androsta-1,4-diene-17β-carbothioic acid S-fluoromethyl ester, and lactose.

2. The pharmaceutical product according to claim 1, wherein Compound (I) is 4-{(1R)-2-[(6-{2-[(2,6-dichlorobenzyl)oxy]ethoxyl}hexyl)amino]-1-hydroxyethyl}-2-(hydroxymethyl)phenol triphenylacetate.

3. The pharmaceutical product according to claim 1 wherein the magnesium stearate is present in an amount of 0.75%.

4. The pharmaceutical product according to claim 1 wherein the magnesium stearate is present in an amount of 1%.

5. The pharmaceutical product according to claim 1 wherein the magnesium stearate is present in an amount of 1.25%.

6. The pharmaceutical product according to claim 1 wherein the magnesium stearate is present in an amount of 1.5%.

7. The pharmaceutical product according to claim 1 wherein the dry powder formulation of Compound (I) and the dry powder formulation of Compound (II) are presented in a form adapted for separate administration.

8. The pharmaceutical product according to claim 1 wherein the dry powder formulation of Compound (I) and the dry powder formulation of Compound (II) are presented in a form adapted for sequential administration.

9. The pharmaceutical product according to claim 1 wherein the dry powder formulation of Compound (I) and the dry powder formulation of Compound (II) are presented in a form adapted for simultaneous administration.

10. The pharmaceutical product according to claim 1 in a form suitable for administration by oral or nasal inhalation.

11. The pharmaceutical product according to claim 3 wherein 4-{(1R)-2-[(6-{2-[(2,6-dichlorobenzyl)oxy]ethoxyl}hexyl)amino]-1-hydroxyethyl}-2-(hydroxymethyl)phenol triphenylacetate is present in a dose of 25 mcg, calculated as the free base.

12. A pharmaceutical product consisting essentially of:
(a) a dry powder formulation consisting essentially of Compound (I), which is 4-{(1R)-2-[(6-{2-[(2,6-dichlorobenzyl)oxy]ethoxyl}hexyl)amino]-1-hydroxyethyl}-2-(hydroxymethyl)phenol, triphenyl acetate present in micronized form and in a dose of 25 mcg, calculated as the free base, and wherein Compound (I) is in admixture with lactose and 0.75 to 1.5% w/w of magnesium stearate, and
(b) a dry powder formulation consisting essentially of Compound (II), which is 6α, 9α-difluoro-17α-[(2-furanylcarbonyl)oxy]-11β-hydroxy-16α-methyl-3-oxo-androsta-1,4-diene-17β-carbothioic acid S-fluoromethyl ester present in a dose of 100 mcg and lactose.

13. The pharmaceutical product according to claim 12 wherein the magnesium stearate is present in an amount of 0.75%.

14. The pharmaceutical product according to claim 12 wherein the magnesium stearate is present in an amount of 1%.

15. The pharmaceutical product according to claim 12 wherein the magnesium stearate is present in an amount of 1.25%.

16. The pharmaceutical product according to claim 12 wherein the magnesium stearate is present in an amount of 1.5%.

17. The pharmaceutical product according to claim 12 wherein the dry powder formulation of Compound (I) and the dry powder formulation of Compound (II) are presented in a form adapted for separate administration.

18. The pharmaceutical product according to claim 12 wherein the dry powder formulation of Compound (I) and the dry powder formulation of Compound (II) are presented in a form adapted for sequential administration.

19. The pharmaceutical product according to claim 12 wherein the dry powder formulation of Compound (I) and the dry powder formulation of Compound (II) are presented in a form adapted for simultaneous administration.

20. A pharmaceutical product consisting essentially of:
(a) a dry powder formulation consisting essentially of Compound (I), which is the 4-{(1 R)-2-[(6-{2-[(2,6-dichlorobenzyl)oxy]ethoxyl}hexyl)amino]-1 -hydroxyethyl}-2-(hydroxymethyl)phenol triphenyl acetate present in micronized form and in a dose of 25 mcg calculated as the free base, and wherein Compound (I) is in admixture with lactose and 0.75 to 1.5% w/w of magnesium stearate, and
(b) a dry powder formulation consisting essentially of Compound (II), which is 6α, 9α-difluoro-17α-[(2-furanylcarbonyl)oxy]-11β-hydroxy-16α-methyl-3-oxo-androsta-1,4-diene-17β-carbothioic acid S-fluoromethyl ester, present in a dose of 200 mcg and lactose.

21. The pharmaceutical product according to claim 20 wherein the magnesium stearate is present in an amount of 0.75%.

22. The pharmaceutical product according to claim 20 wherein the magnesium stearate is present in an amount of 1%.

23. The pharmaceutical product according to claim 20 wherein the magnesium stearate is present in an amount of 1.25%.

24. The pharmaceutical product according to claim 20 wherein the magnesium stearate is present in an amount of 1.5%.

25. The pharmaceutical product according to claim 20 wherein the dry powder formulation of Compound (I) and the dry powder formulation of Compound (II) are presented in a form adapted for separate administration.

26. The pharmaceutical product according to claim 20 wherein the dry powder formulation of Compound (I) and the dry powder formulation of Compound (II) are presented in a form adapted for sequential administration.

27. The pharmaceutical product according to claim 20 wherein the dry powder formulation of Compound (I) and the dry powder formulation of Compound (II) are presented in a form adapted for simultaneous administration.

28. A method for the treatment of a respiratory disease, comprising administering to a patient in need thereof, a pharmaceutical product according to claim 1.

29. A method according to claim 28 wherein the disease is selected from the group consisting of chronic obstructive pulmonary disease, chronic bronchitis, asthma, chronic respiratory obstruction, pulmonary fibrosis, pulmonary emphysema and allergic rhinitis.

30. A method according to claim 28 wherein the disease is asthma.

31. A method according to claim 28 wherein the disease is chronic obstructive pulmonary disease.

32. A method according to claim 28 wherein administration is via inhalation by the mouth or nose.

33. A method according to claim 28 wherein the dry powder formulation of Compound (I) and the dry powder formulation of Compound (II) are administered simultaneously.

34. A method according to claim 28 wherein the pharmaceutical product is administered once per day.

35. A method for the treatment of a respiratory disease, comprising administering to a patient in need thereof, a pharmaceutical product according to claim 12.

36. A method according to claim 35 wherein the disease is selected from the group consisting of chronic obstructive pulmonary disease, chronic bronchitis, asthma, chronic respiratory obstruction, pulmonary fibrosis, pulmonary emphysema and allergic rhinitis.

37. A method according to claim 35 wherein the disease is asthma.

38. A method according to claim 35 wherein the disease is chronic obstructive pulmonary disease.

39. A method according to claim 35 wherein administration is via inhalation by the mouth or nose.

40. A method according to claim 35 wherein the dry powder formulation of Compound (I) and the dry powder formulation of Compound (II) are administered simultaneously.

41. A method according to claim 35 wherein the pharmaceutical product is administered once per day.

42. A method for the treatment of a respiratory disease, comprising administering to a patient in need thereof, a pharmaceutical product according to claim 20.

43. A method according to claim 42 wherein the disease is selected from the group consisting of chronic obstructive pulmonary disease, chronic bronchitis, asthma, chronic respiratory obstruction, pulmonary fibrosis, pulmonary emphysema and allergic rhinitis.

44. A method according to claim 42 wherein the disease is asthma.

45. A method according to claim 42 wherein the disease is chronic obstructive pulmonary disease.

46. A method according to claim 42 wherein administration is via inhalation by the mouth or nose.

47. A method according to claim 42 wherein the dry powder formulation of Compound (I) and the dry powder formulation of Compound (II) are administered simultaneously.

48. A method according to claim 42 wherein the pharmaceutical product is administered once per day.

49. A pharmaceutical product consisting of:
(a) a dry powder formulation of Compound (I), which is 4-{(1 R)-2-[(6-{2-[(2,6-dichlorobenzyl)oxy] ethoxy}hexyl)amino]-1-hydroxyethyl}-2-(hydroxymethyl)phenol or a pharmaceutically acceptable salt thereof, present in micronized form and in a dose selected from the group consisting of 12.5, 25, and 50 mcg, calculated as the free base, and wherein Compound (I) is in admixture with lactose and 0.6 to 2% w/w of magnesium stearate, and
(b) a dry powder formulation of Compound (II), which is 6α, 9α-difluoro-17α-[(2-furanylcarbonyl)oxy]-11β-hydroxy-16α-methyl-3-oxo-androsta-1,4-diene-17β-carbothioic acid S-fluoromethyl ester, and lactose.

50. A pharmaceutical product consisting of:
(a) a dry powder formulation of Compound (I), which is 4-{(1 R)-2-[(6-{2-[(2,6-dichlorobenzyl)oxy] ethoxy}hexyl)amino]-1-hydroxyethyl}-2-(hydroxymethyl)phenol triphenyl acetate present in micronized form and in a dose of 25 mcg, calculated as the free base, and wherein Compound (I) is in admixture with lactose and 0.75 to 1.5% w/w of magnesium stearate, and
(b) a dry powder formulation of Compound (II), which is 6α, 9α-difluoro-17α-[(2-furanylcarbonyl)oxy]-11β-hydroxy-16α-methyl-3-oxo-androsta-1,4-diene-17β-carbothioic acid S-fluoromethyl ester present in a dose of 100 mcg and lactose.

51. A pharmaceutical product consisting of:
(a) a dry powder formulation of Compound (I), which is 4-{(1R)-2-[(6-{2-[(2,6-dichlorobenzyl)oxy] ethoxyl}hexyl)amino]-1-hydroxyethyl}-2-(hydroxymethyl)phenol, triphenyl acetate present in micronized form and in a dose of 25 mcg, calculated as the free base, and wherein Compound (I) is in admixture with lactose and 0.75 to 1.5% w/w of magnesium stearate, and
(b) a dry powder formulation of Compound (II), which is 6α, 9α-difluoro-17α-[(2-furanylcarbonyl)oxy]-11β-hydroxy-16α-methyl-3-oxo-androsta-1,4-diene-17β-carbothioic acid S-fluoromethyl ester, present in a dose of 200 mcg, and is in admixture with lactose.

52. A method for the treatment of a respiratory disease comprising administering to a patient in need thereof a pharmaceutical product according to claim 49.

53. A method according to claim 52 wherein the disease is asthma.

54. A method according to claim 52 wherein the disease is chronic obstructive pulmonary disease.

55. A method according to claim 52 wherein the dry powder formulation of Compound (I) and the dry powder formulation of Compound (II) are administered simultaneously.

56. A method according to claim 52 wherein the pharmaceutical product is administered once per day.

57. A method for the treatment of a respiratory disease comprising administering to a patient in need thereof a pharmaceutical product according to claim 50.

58. A method according to claim 57 wherein the disease is asthma.

59. A method according to claim 57 wherein the disease is chronic obstructive pulmonary disease.

60. A method according to claim 57 wherein the dry powder formulation of Compound (I) and the dry powder formulation of Compound (II) are administered simultaneously.

61. A method according to claim 57 wherein the pharmaceutical product is administered once per day.

62. A method for the treatment of a respiratory disease, comprising administering to a patient in need thereof, a pharmaceutical product according to claim 51.

63. A method according to claim 62 wherein the disease is asthma.

64. A method according to claim 62 wherein the disease is chronic obstructive pulmonary disease.

65. A method according to claim 62 wherein the dry powder formulation of Compound (I) and the dry powder formulation of Compound (II) are administered simultaneously.

66. A method according to claim 62 wherein the pharmaceutical product is administered once per day.

67. The method according to claim 28 wherein Compound (I) and Compound (II) are administered in admixture with each other.

* * * * *